(12) United States Patent
Hadwen et al.

(10) Patent No.: US 11,536,710 B2
(45) Date of Patent: Dec. 27, 2022

(54) DROPLET MICROFLUIDIC DEVICE AND METHODS OF SENSING THE RESULT OF AN ASSAY THEREIN

(71) Applicant: Sharp Life Science (EU) Limited, Oxford (GB)

(72) Inventors: Benjamin James Hadwen, Oxford (GB); Adrian Marc Simon Jacobs, Oxford (GB); Jason Roderick Hector, Oxford (GB); Michael James Brownlow, Oxfordshire (GB); Masahiro Adachi, Osaka (JP); Alison Mary Skinner, Mansfield, MA (US); Mark Childs, Formby Merseyside (GB)

(73) Assignee: Sharp Life Science (EU) Limited, Uxbridge (GB)

( * ) Notice: Subject to any disclaimer, the term of this patent is extended or adjusted under 35 U.S.C. 154(b) by 0 days.

(21) Appl. No.: 17/142,761

(22) Filed: Jan. 6, 2021

(65) Prior Publication Data

US 2021/0148890 A1    May 20, 2021

Related U.S. Application Data

(62) Division of application No. 14/838,781, filed on Aug. 28, 2015, now Pat. No. 11,061,015.

(51) Int. Cl.
*G01N 33/49*    (2006.01)
*C12Q 1/6844*    (2018.01)
(Continued)

(52) U.S. Cl.
CPC .... *G01N 33/4905* (2013.01); *B01L 3/502792* (2013.01); *C12Q 1/6844* (2013.01);
(Continued)

(58) Field of Classification Search
CPC .. C12Q 1/6816; C12Q 1/6874; C12Q 1/6844; C12Q 2563/116; C12Q 2563/519;
(Continued)

(56) References Cited

U.S. PATENT DOCUMENTS

| | | |
|---|---|---|
| 4,221,865 A | 9/1980 | Dubczak et al. |
| 4,221,866 A | 9/1980 | Cotter |

(Continued)

FOREIGN PATENT DOCUMENTS

| | | |
|---|---|---|
| EP | 2 514 529 A2 | 10/2012 |
| EP | 2 741 120 A1 | 6/2014 |

(Continued)

OTHER PUBLICATIONS

"Digital microfluidics: is a true lab-on-a-chip possible?", R.B. Fair, Microfluid Nanofluid (2007) 3:245-281).
(Continued)

*Primary Examiner* — Mayla Gonzalez Ramos
(74) *Attorney, Agent, or Firm* — Renner, Otto, Boisselle & Sklar, LLP

(57) ABSTRACT

A method of determining the result of an assay in a microfluidic device includes the steps of: dispensing a sample droplet onto a first portion of an electrode array of the microfluidic device; dispensing a reagent droplet onto a second portion of the electrode array of the microfluidic device; controlling actuation voltages applied to the electrode array to mix the sample droplet and the reagent droplet into a product droplet; sensing a dynamic property of the product droplet; and determining an assay of the sample droplet based on the sensed dynamic property. The dynamic property is a physical property of the product droplet that influences a transport property of the product droplet on the electrode array. Example dynamic properties of the product droplet include the moveable state, split-able state, and
(Continued)

viscosity based on droplet properties. The method may be used to perform an amoebocyte lysate (LAL) assay.

19 Claims, 22 Drawing Sheets

(51) Int. Cl.
    *B01L 3/00*              (2006.01)
    *G01N 33/579*        (2006.01)
    *C12Q 1/6816*        (2018.01)
    *G01N 30/60*         (2006.01)
    *G01N 30/88*         (2006.01)

(52) U.S. Cl.
CPC ..... *B01L 2200/14* (2013.01); *B01L 2200/148* (2013.01); *B01L 2300/0645* (2013.01); *B01L 2300/0819* (2013.01); *B01L 2300/1822* (2013.01); *B01L 2400/0427* (2013.01); *B01L 2400/0677* (2013.01); *C12Q 1/6816* (2013.01); *G01N 30/6095* (2013.01); *G01N 33/579* (2013.01); *G01N 2030/8813* (2013.01)

(58) Field of Classification Search
CPC ........ C12Q 2565/607; C12Q 2565/629; B01L 3/502715; B01L 3/502792; B01L 3/50273; B01L 2300/0645; B01L 2300/0819; B01L 2300/1822; B01L 2400/0427; B01L 2400/0677; B01L 2200/14; B01L 2200/148; G01N 27/44791
See application file for complete search history.

(56) References Cited

U.S. PATENT DOCUMENTS

| | | | |
|---|---|---|---|
| 4,273,557 A | 6/1981 | Juranas | |
| 4,276,050 A | 6/1981 | Firca et al. | |
| 4,495,294 A | 1/1985 | Nakahara et al. | |
| 6,565,727 B1 | 5/2003 | Shenderov | |
| 6,911,132 B2 | 6/2005 | Pamula et al. | |
| 7,163,612 B2 | 1/2007 | Sterling et al. | |
| 7,816,121 B2 * | 10/2010 | Pollack ............. | B01L 3/502761 435/293.1 |
| 8,653,832 B2 | 2/2014 | Hadwen et al. | |
| 2007/0241068 A1 | 10/2007 | Pamula et al. | |
| 2010/0194408 A1 | 8/2010 | Sturmer et al. | |
| 2011/0104725 A1 | 5/2011 | Pamula et al. | |
| 2013/0288254 A1 | 10/2013 | Pollack et al. | |
| 2014/0197028 A1 | 7/2014 | Jacobs et al. | |
| 2015/0060272 A1 | 3/2015 | Blidner et al. | |

FOREIGN PATENT DOCUMENTS

| | | |
|---|---|---|
| EP | 2759342 | 7/2014 |
| WO | WO 9408221 | 4/1994 |
| WO | WO 2008/101194 A2 | 8/2008 |
| WO | WO 2009135205 | 11/2009 |
| WO | WO 2017/038064 A1 | 3/2017 |
| WO | WO 2017038063 | 3/2017 |

OTHER PUBLICATIONS

"Integration and detection of biochemical assays in digital microfluidic Lab-on-a-Chip devices", Malic et al, Lab Chip, 2010, 10, 418-431.
"Modelling the Fluid Dynamics of Electrowetting on Dielectric (Ewod)", Walker and Shapiro, Journal of MicroElectroMechanical Systems, vol. 15, No. 4, Aug 2006.
"Droplet microfluidics", Teh et al. Lab Chip 2008 8 198-202.
"The limulus clotting reaction", Iwanaga, Curr: Opin. Immunol. 5:74-82 (1993).
"Lipopolysaccharide-sensitive serine-protease zymogen (factor C) found in Limulus hemocytes", Nakamura et al., Eur. J.Biochem. 154: 511-521 (1986).
Muta et al.,J. Biochem. 101:1321-1330 (1987).
Ho et al., Biochem. Mol. Biol. Int. 29: 687-694 (1993).
Nelson, Wyatt, A Micro Extensional Filament Rheometer Enabled by EWOD, Proc. Int. Conf. MEMS 2010, Jan. 2010, pp. 75-78.
Lin et al: "Micro-viscometer based on electrowetting on dielectric", Electrochimica A, Elsevier Science Publishers, Barking, GB, vol. 52, No. 8, Jan. 30, 2007 (Jan. 30, 2007), pp. 2876-2883.
Royal Matthew White et al: "Droplet-Based Sensing: Optical Microresonator Sensors Embedded in Digital Electrowetting Microfluidics Systems", IEEE Service Center, New York, NY, US, vol. 13, No. 12, Dec. 1, 2013 (Dec. 1, 2013), pp. 4733-4742.
Malic L et al: "Biochip functionalization using electrowetting-on-dielectric digital microfluidics for surface plasmon resonance imaging detection of DNA hybridization," Biosensors and Bioelectronics, Elsevier Science Ltd. UK, Amsterdam, NL, vol. 24, No. 7, Mar. 15, 2009 (Mar. 15, 2009), pp. 2218-2224.
Schertzer M J et al: "Using capacitance measurements in EWOD devices to identify fluid composition and control droplet mixing", Sensors and Actuators B: Chemical: International Journal Devoted to Research and Development of Physical and Chemical Transducers, Elsevier BV, NL, vol. 145, No. 1, Mar. 4, 2010 (Mar. 4, 2010), pp. 340-347.
Xize Niu et al: "Real-time detection, control and sorting of microfluidic droplets", Biomicrofluidics, Oct. 3, 2007 Oct. 3, 2007), pp. 044101-1, XP055143766, DOI: 10.1063/1.2795392 Retrieved from the Internet: URL:http://dx.doi.org/10.1063/1.2795392.
Xiaoge Qu et al.: "A new method based on gelation of tachypleus amebocyte lysate for detection of *Escherichia coli*form using a series piezoelectric quartz crystal sensor." Analytica Chimica Acta. vol. 374, No. 1, pp. 47-52, Nov. 1, 1998.
Kondoh Jun et al.: "Measurements of blood coagulation using digital micro-fluidic system based on surface acoustic wave devices" 2015 International Conference on Quality in Research (QiR), Lombok, 2015, pp. 19-22, doi: 10.1109/QiR.2015.7374886, http://ieeexplore.ieee.org/stamp/stamp.jsp?tp=&arnumber=7374886&isnumber=7374873 (Abstract only).

* cited by examiner

DROPLET MICROFLUIDIC DEVICE AND METHODS OF SENSING THE RESULT OF AN ASSAY THEREIN

RELATED APPLICATION DATA

This application is a divisional application of U.S. application Ser. No. 14/838,781 filed on Aug. 28, 2015, the content of which is incorporated herein by reference.

TECHNICAL FIELD

The present invention relates to droplet microfluidic devices, and in a particular aspect to Electro-wetting on Dielectric (EWOD) devices and more specifically to Active Matrix Electro-wetting-On-Dielectric (AM-EWOD), and further relates to methods of sensing a dynamic property of one or more droplets on such devices in order to determine the result of a chemical or bio-chemical test.

BACKGROUND ART

Electrowetting on dielectric (EWOD) is a well known technique for manipulating droplets of fluid by application of an electric field. Active Matrix EWOD (AM-EWOD) refers to implementation of EWOD in an active matrix array incorporating transistors, for example by using thin film transistors (TFTs). It is thus a candidate technology for digital microfluidics for lab-on-a-chip technology. An introduction to the basic principles of the technology can be found in "Digital microfluidics: is a true lab-on-a-chip possible?", R. B. Fair, Microfluid Nanofluid (2007) 3:245-281).

FIG. 1 shows a part of a conventional EWOD device in cross section. The device includes a lower substrate 72, the uppermost layer of which is formed from a conductive material which is patterned so that a plurality of array element electrodes 38 (e.g., 38A and 38B in FIG. 1) are realized. The electrode of a given array element may be termed the element electrode 38. The liquid droplet 4, including a polar material (which is commonly also aqueous and/or ionic), is constrained in a plane between the lower substrate 72 and a top substrate 36. A suitable gap between the two substrates may be realized by means of a spacer 32, and a non-polar fluid 34 (e.g. oil) may be used to occupy the volume not occupied by the liquid droplet 4. An insulator layer 20 disposed upon the lower substrate 72 separates the conductive element electrodes 38A, 38B from a first hydrophobic coating 16 upon which the liquid droplet 4 sits with a contact angle 6 represented by 8. The hydrophobic coating is formed from a hydrophobic material (commonly, but not necessarily, a fluoropolymer).

On the top substrate 36 is a second hydrophobic coating 26 with which the liquid droplet 4 may come into contact. Interposed between the top substrate 36 and the second hydrophobic coating 26 is a reference electrode 28.

The contact angle θ 6 is defined as shown in FIG. 1, and is determined by the balancing of the surface tension components between the solid-liquid ($\gamma_{SL}$), liquid-gas ($\gamma_{LG}$) and non-ionic fluid ($\gamma_{SG}$) interfaces, and in the case where no voltages are applied satisfies Young's law, the equation being given by:

$$\cos\theta = \frac{\gamma_{SG} - \gamma_{SL}}{\gamma_{LG}} \quad \text{(equation 1)}$$

In operation, voltages termed the EW drive voltages, (e.g. $V_T$, $V_0$ and $V_{00}$ in FIG. 1) may be externally applied to different electrodes (e.g. reference electrode 28, element electrodes 38, 38A and 38B, respectively). The resulting electrical forces that are set up effectively control the hydrophobicity of the hydrophobic coating 16. By arranging for different EW drive voltages (e.g. $V_0$ and $V_{00}$) to be applied to different element electrodes (e.g. 38A and 38B), the liquid droplet 4 may be moved in the lateral plane between the two substrates 72 and 36.

U.S. Pat. No. 6,565,727 (Shenderov, issued May 20, 2003) discloses a passive matrix EWOD device for moving droplets through an array.

U.S. Pat. No. 6,911,132 (Pamula et al., issued Jun. 28, 2005) discloses a two dimensional EWOD array to control the position and movement of droplets in two dimensions.

U.S. Pat. No. 6,565,727 further discloses methods for other droplet operations including the splitting and merging of droplets, and the mixing together of droplets of different materials.

U.S. Pat. No. 7,163,612 (Sterling et al., issued Jan. 16, 2007) describes how TFT based thin film electronics may be used to control the addressing of voltage pulses to an EWOD array by using circuit arrangements very similar to those employed in AM display technologies.

The approach of U.S. Pat. No. 7,163,612 may be termed "Active Matrix Electrowetting on Dielectric" (AM-EWOD). There are several advantages in using TFT based thin film electronics to control an EWOD array, namely:

- Electronic driver circuits can be integrated onto the lower substrate 72.
- TFT-based thin film electronics are well suited to the AM-EWOD application. They are cheap to produce so that relatively large substrate areas can be produced at relatively low cost.
- TFTs fabricated in standard processes can be designed to operate at much higher voltages than transistors fabricated in standard CMOS processes. This is significant since many EWOD technologies require electro-wetting voltages in excess of 20V to be applied.

A disadvantage of U.S. Pat. No. 7,163,612 is that it does not disclose any circuit embodiments for realizing the TFT backplane of the AM-EWOD.

US application 2010/0194408 (Sturmer et al., published Aug. 5, 2010) describes a method, circuit and apparatus for detecting capacitance on a droplet actuator, inter alia, for determining the presence, partial presence or absence of a droplet at an electrode.

U.S. Pat. No. 8,653,832 (Hadwen et al., issued Feb. 18, 2014) describes how an impedance (capacitance) sensing function can be incorporated into the array element of an AM-EWOD device. The impedance sensor may be used for determining the presence and size of liquid droplets present at each electrode in the array.

It is well known that optical methods may be used for the detection of biochemical assays in EWOD devices, for example "Integration and detection of biochemical assays in digital microfluidic Lab-on-a-Chip devices", Malic et al, Lab Chip, 2010, 10, 418-431.

The physical dependence of droplet dynamic properties, e.g. speed of movement, characteristics of splitting, and the like, of EWOD devices are found to be a function of the device geometry and droplet properties as described for example in "Modelling the Fluid Dynamics of Electrowetting on Dielectric (EWOD)", Walker and Shapiro, Journal of MicroElectroMechanical Systems, Vol. 15, No. 4, August 2006.

Droplet microfluidic systems based on principles of operation other than EWOD are also known. A review of the field is given in "Droplet microfluidics", The et al. Lab Chip 2008 8 198-202.

Bacterial endotoxins, also known as pyrogens, are the fever-producing by-products of gram-negative bacteria and can be dangerous or even deadly to humans. Symptoms of infection and presence of endotoxin range from fever, in mild cases, to death.

Cells from the hemolymph of the horseshoe crab (amebocytes) contain an endotoxin-binding protein (Factor C) that initiates a series of complex enzymatic reactions resulting in clot formation when the cells are in contact with endotoxin (reviewed in Iwanaga, Curr: Opin. Immunol. 5:74-82 (1993)). The endotoxin-mediated activation of an extract of these cells, i.e. amebocyte lysate, is well-understood and has been thoroughly documented in the art, see, for example, Nakamura et al., Eur. J. Biochem. 154: 511-521 (1986); Muta et al.,]. Biochem. 101:1321-1330 (1987); and Ho et al., Biochem. Mol. Biol. Int. 29: 687-694 (1993). This phenomenon has been exploited in bioassays to detect endotoxin in a variety of test samples, including human and animal pharmaceuticals, biological products, research products, and medical devices. The horseshoe crab Limuluspolyphemus is particularly sensitive to endotoxin. Accordingly, the blood cells from this horseshoe crab, termed "Limulus amebocyte lysate" or "LAL," are employed widely in endotoxin assays of choice because of their sensitivity, specificity, and relative ease for avoiding interference by other components that may be present in a sample. See, e.g., U.S. Pat. No. 4,495,294 (Nakahara et al., issued Jan. 22, 1985), U.S. Pat. No. 4,276,050 (Firca et al., issued Jun. 30, 1981), U.S. Pat. No. 4,273,557 (Juranas, issued Jun. 16, 1981), U.S. Pat. No. 4,221,865 (Dubczak et al., issued Sep. 9, 1980), and U.S. Pat. No. 4,221,866 (Cotter, issued Sep. 9, 1980). LAL, when combined with a sample containing bacterial endotoxin, reacts with the endotoxin to produce a product, for example, a gel clot or chromogenic product, that can be detected, for example, either visually, or by the use of an optical detector.

It is also well known that LAL may be used for the detection of (1,3)-beta-D-glucans, and chemistries have been developed for performing LAL based assays that may be specific to either endotoxin or glucan detection.

Many methods of nucleic acid amplification, such as Polymerase Chain Reaction (PCR), are very well known. Typically, a target nucleic acid sequence may be amplified selectively by mixing the sample with appropriately designed primers. Conventionally, the outcome of the assay may be sensed optically, for example by measuring the fluorescence properties of the assay product.

Exponential amplification may be achieved either by means of thermal cycling (as is the case with PCR) or at constant temperature, so-called isothermal amplification. Nucleic acid amplification may be used to convert a small number of strands of DNA having the target sequence into a very large number of strands according to an exponential process, typically until all the reagents are used up.

Coagulation (clotting) is the process by which blood changes from a liquid to a gel. It potentially results in hemostasis, the cessation of blood loss from a damaged vessel, followed by repair. The mechanism of coagulation involves activation, adhesion, and aggregation of platelets along with deposition and maturation of fibrin. Disorders of coagulation are disease states which can result in bleeding (hemorrhage or bruising) or obstructive clotting (thrombosis).

Anticoagulant therapy, including conventional agents and a variety of new oral, fast-acting drugs, is prescribed for millions of patients annually. Each anticoagulant varies in its effect on routine and specialty coagulation assays, and each drug may require distinct laboratory assay(s) to measure drug concentration or activity.

Coagulation assays may work by mixing a quantity of a sample (blood, or derived from blood) with a chemical that has the effect of causing the blood to coagulate (clot). Alternatively, such assays may mix the sample with substances that prevent coagulation. In each case either the change in viscosity or the change to a solid phase (clotting) of blood may be measured to determine the result of the assay.

SUMMARY OF INVENTION

A droplet microfluidic device, for example an AM-EWOD device, is used to perform an assay in a droplet format.

According to a first aspect of the invention, the sample and reagent droplets are manipulated in droplet format by the droplet microfluidic device. A calibration curve, comprising a set of calibration data, is performed on device by reacting a series of one or more reference droplets. The reference droplets may be generated internally within the microfluidic device, and multiple reference droplets of different concentration may be generated, for example, by serial dilution. The calibration curve may also be generally referred to as a standard curve in some contexts, and whilst in the description that follows the term "calibration curve" is generally used, this may be considered to equate to a standard curve in contexts where that is applicable.

According to a second aspect of the invention, the result of the assay may result in the change of a dynamic property (for example the ability to move or split a droplet, or the maximum speed of movement) of one or more droplets in the device.

The invention embodies various exemplary means by which a dynamic property of a droplet may be changed according to a chemical or bio-chemical process that occurs within the droplet. For example, there may be a change in the viscosity of the droplet, the droplet may undergo a phase change from a liquid to a gel or solid phase, or there may a precipitation or partial precipitation of solid matter within the droplet, or there may be the formation or change of a colloid or emulsion within the droplet.

The invention further embodies exemplary means by which a droplet dynamic property may be sensed, for example by means of a droplet sensing function integrated into the AM-EWOD device. Such a sensor may be used, for example, to measure the position, centroid or perimeter of the droplet and its change in time.

Additionally the invention describes varies integrated means of calibrating the detected quantity, for example by comparing a dynamic property of the droplet to reference droplets or assay products, or by performing differential measurements of a dynamic property of one or more droplets.

Exemplary assays where the assay product may be sensed in this way have been embodied and include assays based on LAL for the detection of either or both of bacterial endotoxins of (1,3)-beta-D glucans, nucleic acid amplification assays, precipitation assays, assays resulting in protein crystallization, or assays that result in a phase change of the droplet material.

An advantage of the invention is that it provides for an integrated means of detecting the result of an assay that is label free and does not require the use of optical techniques to interrogate the droplet. This may be achieved by adding minimal additional complexity to the AM-EWOD device platform, and the results of the assay may be determined simply by making changes to the application software. Such a technique may result in a considerably simplified system resulting in a smaller, simpler and lower cost cartridge and reader, and a system that is very easy to use for a non-specialist operator.

BRIEF DESCRIPTION OF DRAWINGS

In the annexed drawings, like references indicate like parts or features.

Figure 1:
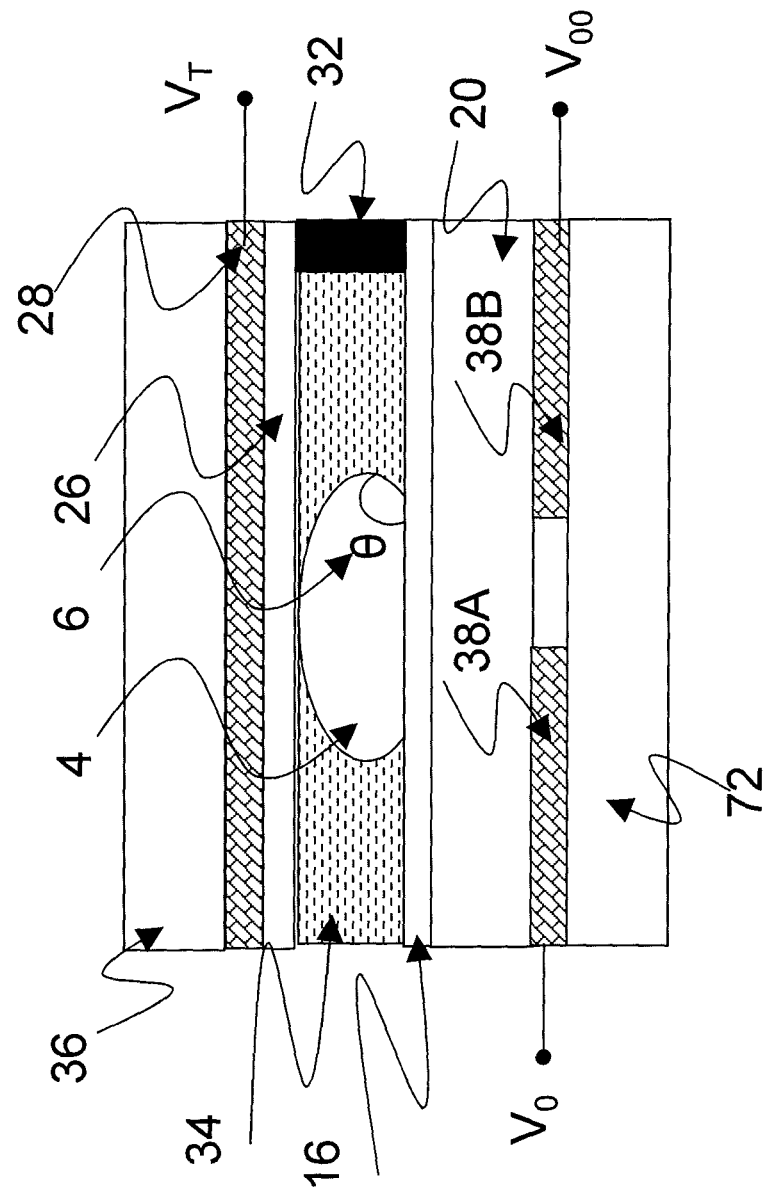
FIG. 1 is a schematic diagram depicting a conventional EWOD device in cross-section.

DESCRIPTION OF REFERENCE NUMERALS 4 liquid droplet
4B sample droplet
4A, 4C reagent droplet
4D product droplet
4E Intermediate product droplet
4F LAL reagent droplet
4P, 4Q, 4R, 4S Reference droplets
4T droplet
4U Negative control standard droplet
4V Controlled standard endotoxin droplet
4X Starting reference droplet
4Y Water droplet
4Z Further droplet
4AA Positive control reference droplet
4AB Positive control product droplet
6 contact angle θ
8 Sample test
10 Calibration tests
12 Negative control test
14 Reaction
16 First hydrophobic coating
20 Insulator layer
26 Second hydrophobic coating
28 Reference electrode
32 Spacer
34 Non-polar fluid
36 Top substrate
38/38A and 38B Array Element Electrodes
40 Reader
40A/40B Electrical load
41 AM-EWOD device
42 Electrode array
44 Cartridge
46 Actuation circuit
48 Sensing circuit
50 Control electronics
52 Application software
72 Lower Substrate 74 Thin film electronics
76 Row driver circuit
78 Column driver circuit
80 Serial interface
82 Connecting wires
83 Voltage supply interface
84 Array element circuit
86 Column detection circuit
88 Sensor row addressing
90 Calibration curve
92 Measurement result

DETAILED DESCRIPTION OF INVENTION

Figure 2:
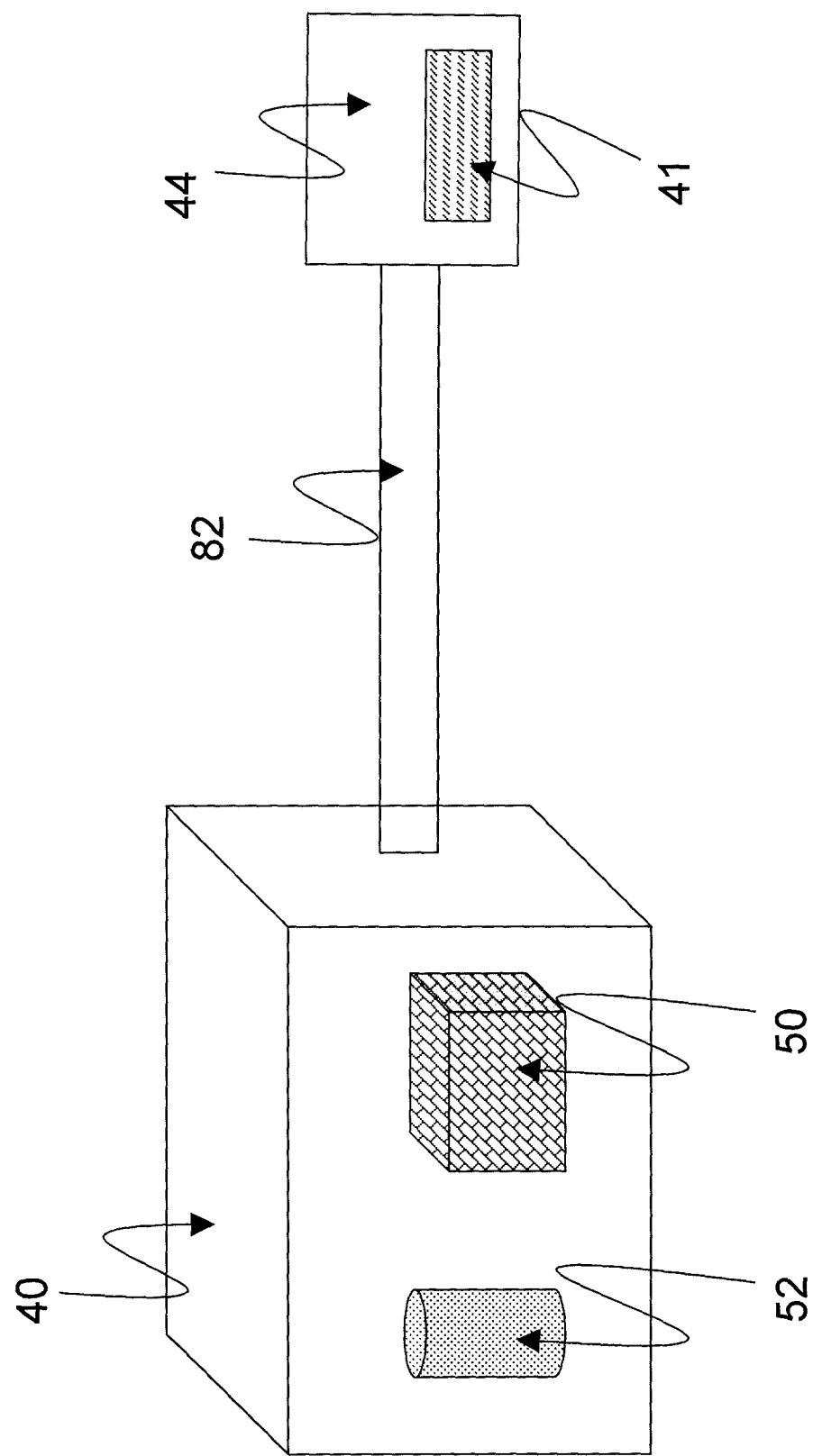
FIG. 2 shows an exemplary assay measurement system according to a first embodiment of the invention.

FIG. 2 shows an exemplary assay measurement system according to a first embodiment of the present invention. The measurement system includes two parts such as a reader 40 and a cartridge 44. The cartridge 44 may contain a microfluidic device, such as an AM-EWOD device 41, as well as (not shown) fluid input ports into the device and an electrical connection. The fluid input ports may perform the function of inputting fluid into the AM-EWOD device 41 and generating droplets 4 within the device, for example by dispensing from input reservoirs as controlled by electro-wetting. 15. As further detailed below, the microfluidic device includes an electrode array configured to receive the inputted fluid droplets.

The assay measurement system further may include a controller configured to control actuation voltages applied to the electrode array of the microfluidic device to perform manipulation operations to the fluid droplets. For example, the reader 40 may contain such a controller configured as control electronics 50 and a database 52 storing application software. The database 52 may be stored on any suitable computer-readable medium, such as a memory or like storage device. The application software 52 may contain computer code to perform some or all of the following functions when executed by the control electronics:

Define the appropriate timing signals to manipulate liquid droplets 4 on the AM-EWOD device 41.
Interpret input data representative of sensor information measured by a sensor associated with the AM-EWOD device 41, including computing the locations, sizes, centroids and perimeters of liquid droplets on the AM-EWOD device 41.
Use calculated sensor data to define the appropriate timing signals to manipulate liquid droplets on the AM-EWOD device 41, i.e. acting in a feedback mode.
A graphical user interface (GUI) whereby the user may program commands such as droplet operations (e.g. move a droplet), assay operations (e.g. perform an assay), and which may report the results of such operations to the user.

The control electronics 50 may supply the control actuation voltages applied to the electrode array of the microfluidics device, such as required voltage and timing signals to perform droplet manipulation operations and sense liquid droplets 4 on the AM-EWOD device 41. The control electronics further may execute the application software to generate and output results data for a result of the assay. The results data may be outputted in various ways, such as being stored in the storage device storing database 52 or another suitable storage device. The results data further may be outputted, for example, via the GUI for display on any suitable display device, and/or outputted as an audio signal such as through a speaker system or like device.

The reader 40 and cartridge 44 may be connected together whilst in use, for example by a cable of connecting wires 82, although various other methods of making electrical communication may be used as is well known.

Figure 3:
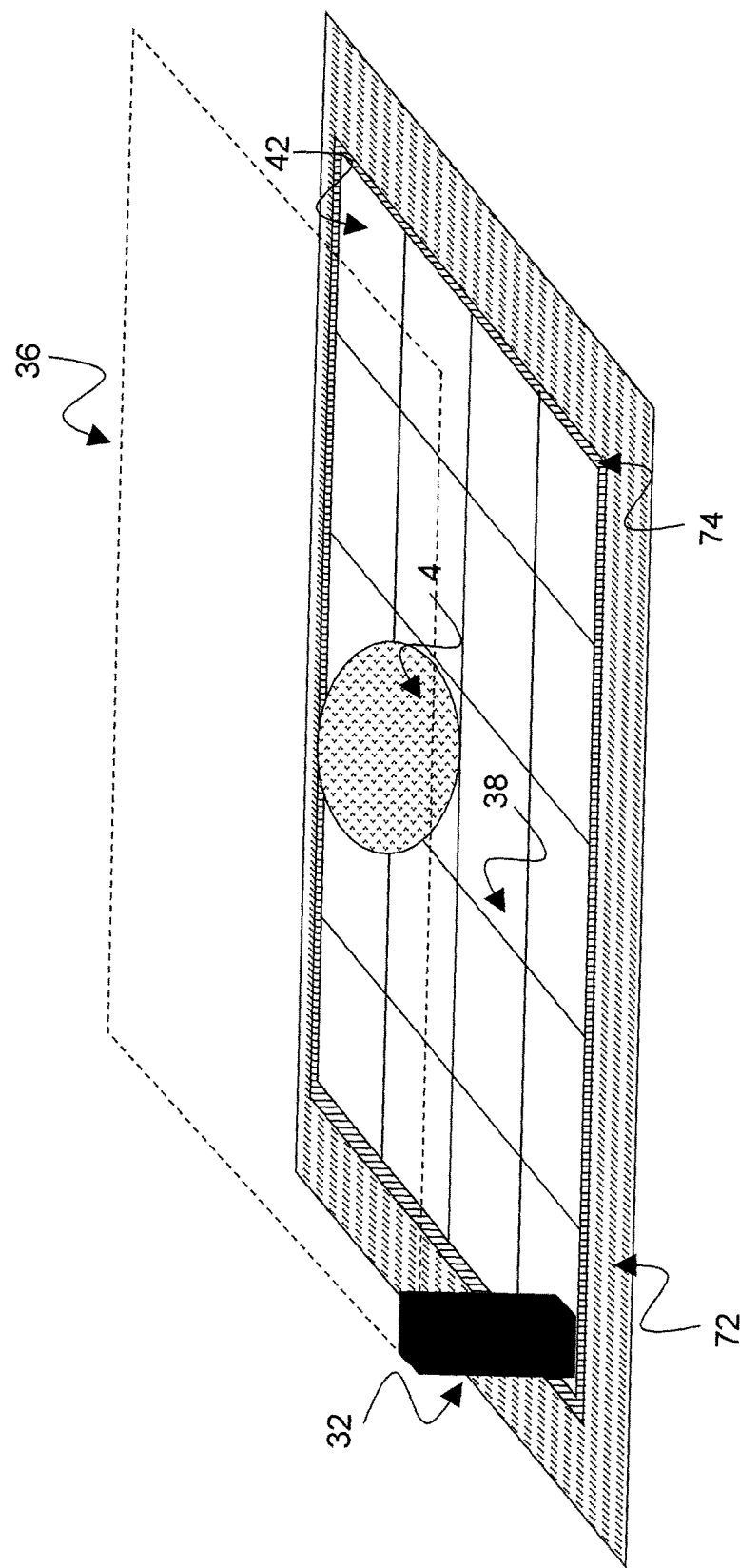
FIG. 3 is a schematic diagram depicting an AM-EWOD device in schematic perspective in accordance with a first embodiment of the invention.

FIG. 3 is a schematic diagram depicting an AM-EWOD device 41 that may form part of the cartridge 44 in accordance with an exemplary embodiment of the invention. The AM-EWOD device 41 has a lower substrate 72 with thin film electronics 74 disposed upon the lower substrate 72. The thin film electronics 74 are arranged to drive the array element electrodes 38. A plurality of array element electrodes 38 are arranged in an electrode array 42, having X by Y elements where X and Y may be any integer. A liquid droplet 4 which may include any polar liquid and which typically may be aqueous, is enclosed between the lower substrate 72 and a top substrate 36, although it will be appreciated that multiple liquid droplets 4 can be present.

Figure 4:
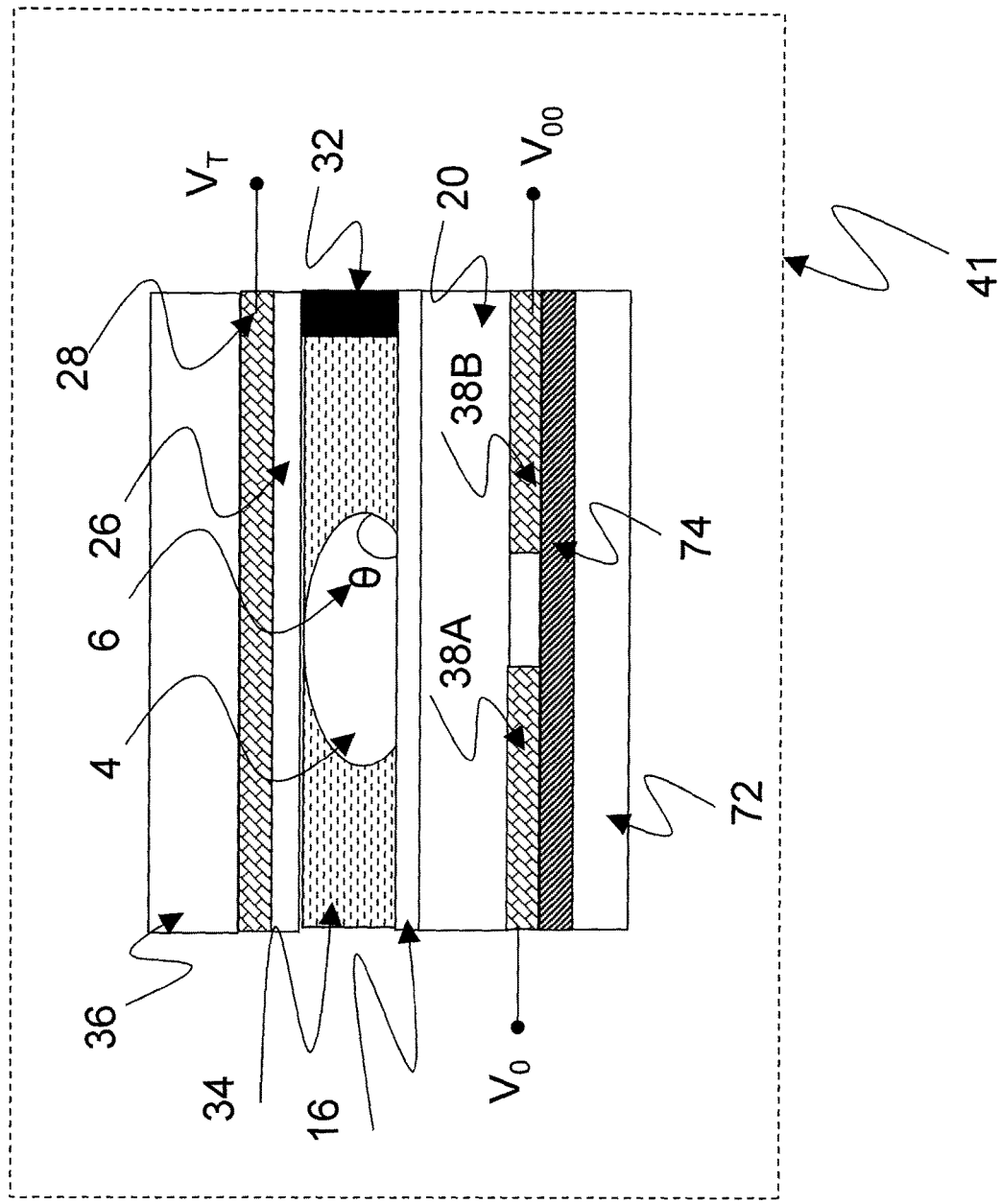
FIG. 4 shows a cross section through some of the array elements of the exemplary AM-EWOD device of FIG. 3.

FIG. 4 is a schematic diagram depicting a pair of the array element electrodes 38A and 38B in cross section that may be utilized in the electrode array 42 of the AM-EWOD device 41 of FIG. 3. The device configuration is similar to the conventional configuration shown in FIG. 1, with the AM-EWOD device 41 further incorporating the thin-film electronics 74 disposed on the lower substrate 72. The uppermost layer of the lower substrate 72 (which may be considered a part of the thin film electronics layer 74) is patterned so that a plurality of the array element electrodes 38 (e.g. specific examples of array element electrodes are 38A and 38B in FIG. 4) are realized. The term element electrode 38 may be taken in what follows to refer both to the physical electrode structure 38 associated with a particular array element, and also to the node of an electrical circuit directly connected to this physical structure. The reference electrode 28 is shown in FIG. 4 disposed upon the top substrate but may alternatively be disposed upon the lower substrate 72 to realize an in-plane reference electrode 28 geometry. The term reference electrode 28 may also be taken in what follows to refer to both or either of the physical electrode structure and also to the node of an electrical circuit directly connected to this physical structure.

Figure 5B:
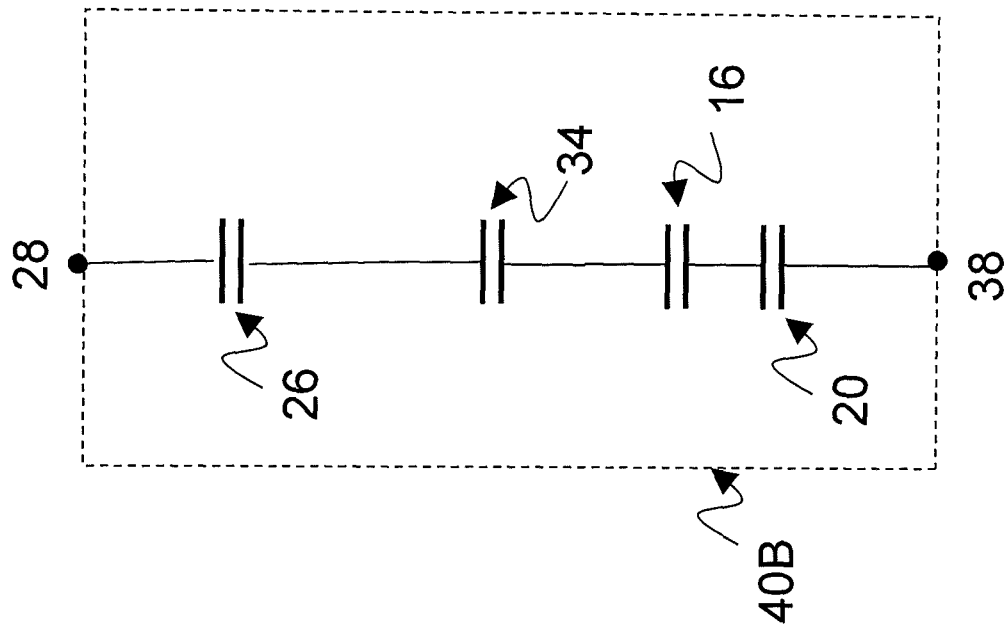
FIG. 5B shows a circuit representation of the electrical load presented at the element electrode when no liquid droplet is present.
Figure 5A:
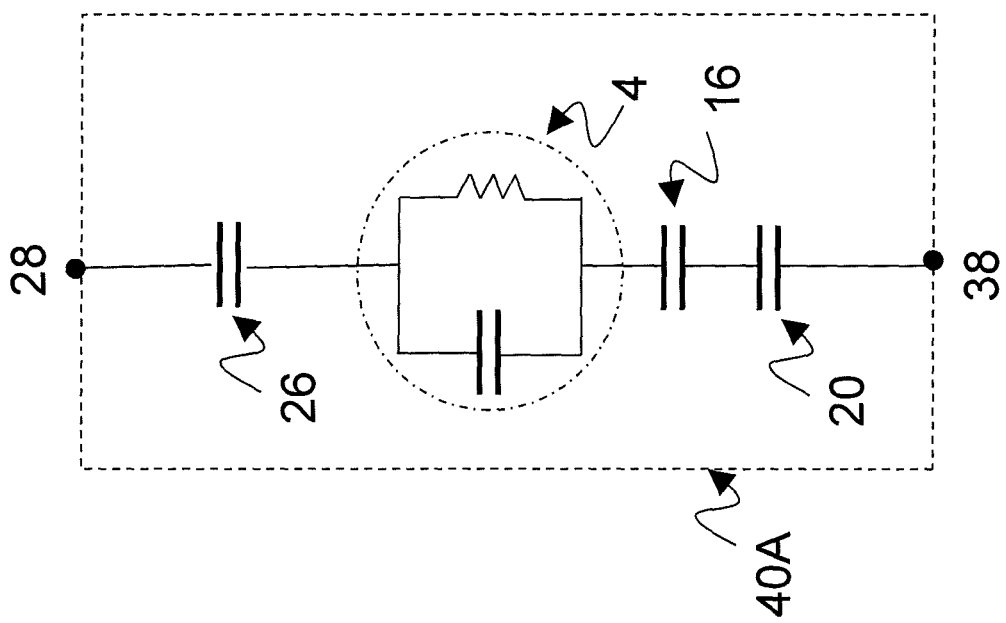
FIG. 5A shows a circuit representation of the electrical load presented at the element electrode when a liquid droplet is present.

FIG. 5A shows a circuit representation of the electrical load 40A between the element electrode 38 and the reference electrode 28 in the case where a liquid droplet 4 is present. The liquid droplet 4 can usually be modeled as a resistor and capacitor in parallel. Typically, the resistance of the droplet will be relatively low (e.g. if the droplet contains ions) and the capacitance of the droplet will be relatively high (e.g. because the relative permittivity of polar liquids is relatively high, e.g. ~80 if the liquid droplet is aqueous). In many situations the droplet resistance is relatively small, such that at the frequencies of interest for electro-wetting, the liquid droplet 4 may function effectively as an electrical short circuit. The hydrophobic coatings 16 and 26 have electrical characteristics that may be modelled as capacitors, and the insulator 16 may also be modelled as a capacitor. The overall impedance between the element electrode 38 and the reference electrode 28 may be approximated by a capacitor whose value is typically dominated by the contribution of the insulator 20 and hydrophobic coatings 16 and 26 contributions, and which for typical layer thicknesses and materials may be on the order of a pico-Farad in value.

FIG. 5B shows a circuit representation of the electrical load 40B between the element electrode 38 and the reference electrode 28 in the case where no liquid droplet 4 is present. In this case the liquid droplet 4 components are replaced by a capacitor representing the capacitance of the non-polar fluid 34 which occupies the space between the top and lower substrates. In this case the overall impedance between the element electrode 38 and the reference electrode 28 may be approximated by a capacitor whose value is dominated by the capacitance of the non-polar fluid and which is typically small, on the order of femto-Farads.

For the purposes of driving and sensing, the electrical load 40A/40B overall functions in effect as a capacitor, whose value depends on whether a liquid droplet 4 is present or not at a given element electrode 38. In the case where a droplet is present, the capacitance is relatively high (typically of order pico-Farads), whereas if there is no liquid droplet 4 present the capacitance is low (typically of order femto-Farads). If a droplet partially covers a given electrode 38 then the capacitance may approximately represent the extent of coverage of the element electrode 38 by the liquid droplet 4.

Figure 6:
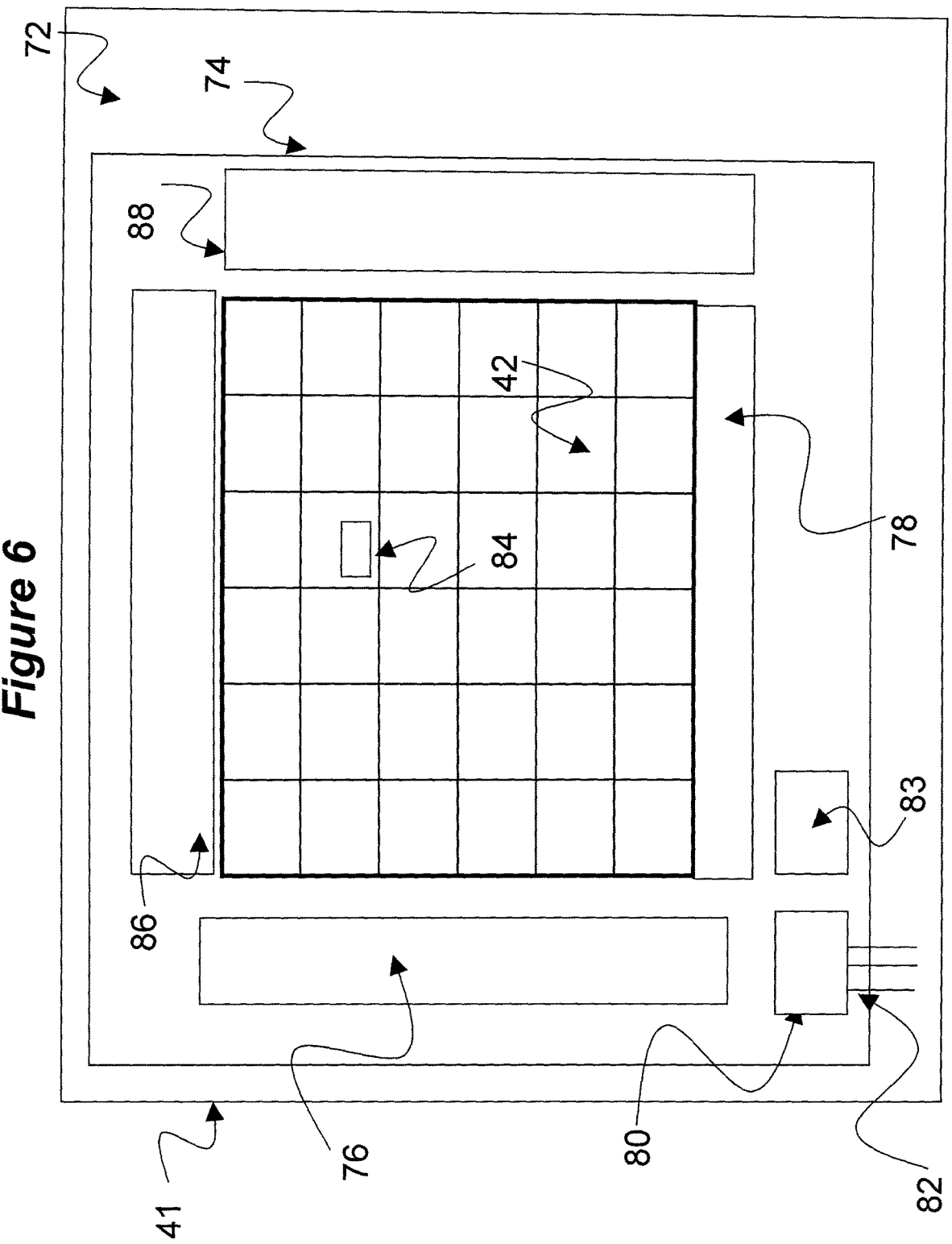
FIG. 6 is a schematic diagram depicting the arrangement of thin film electronics in the exemplary AM-EWOD device of FIG. 3 according to a first embodiment of the invention.

FIG. 6 is a schematic diagram depicting an exemplary arrangement of thin film electronics 74 upon the lower substrate 72. Each element of the electrode array 42 contains an array element circuit 84 for controlling the electrode potential of a corresponding element electrode 38. Integrated row driver 76 and column driver 78 circuits are also implemented in thin film electronics 74 to supply control signals to the array element circuit 84. The array element circuit 84 may also contain a sensing capability for detecting the presence or absence of a liquid droplet 4 in the location of the array element. Integrated sensor row addressing 88 and column detection circuits 86 may further be implemented in thin film electronics for the addressing and readout of the sensors in each array element.

A serial interface 80 may also be provided to process a serial input data stream and facilitate the programming of the required voltages to the element electrodes 38 in the array 42. A voltage supply interface 83 provides the corresponding supply voltages, top substrate drive voltages, and other requisite voltage inputs as further described herein. The number of connecting wires 82 between the lower substrate 72 and external drive electronics, power supplies and any other components can be made relatively few, even for large array sizes. Optionally, the serial data input may be partially parallelized. For example, if two data input lines are used the first may supply data for columns 1 to X/2, and the second for columns (1+X/2) to M with minor modifications to the column driver 78 circuits. In this way the rate at which data can be programmed to the array is increased, which is a standard technique used in Liquid Crystal Display driving circuitry.

Generally, an exemplary AM-EWOD device 41 that includes thin film electronics 74 is configured as follows. The AM-EWOD device 41 includes a reference electrode 28 (which, optionally, could be an in-plane reference electrode 28) and a plurality of array elements, each array element including an array element electrode (e.g., array element electrodes 38).

Relatedly, the AM-EWOD device 41 is configured to perform a method of actuating liquid droplets by controlling an electro-wetting voltage to be applied to a plurality of array elements. The AM-EWOD device 41 contains a reference electrode 28 and a plurality of array elements, each array element including an array element electrode 38. The electro-wetting voltage at each array element is defined by a potential difference between the array element electrode 38 and the reference electrode 28. The method of controlling the electro-wetting voltage at a given array element typically includes the steps of supplying a voltage to the array element electrode 38, and supplying a voltage to the reference electrode 28.

Figure 7:
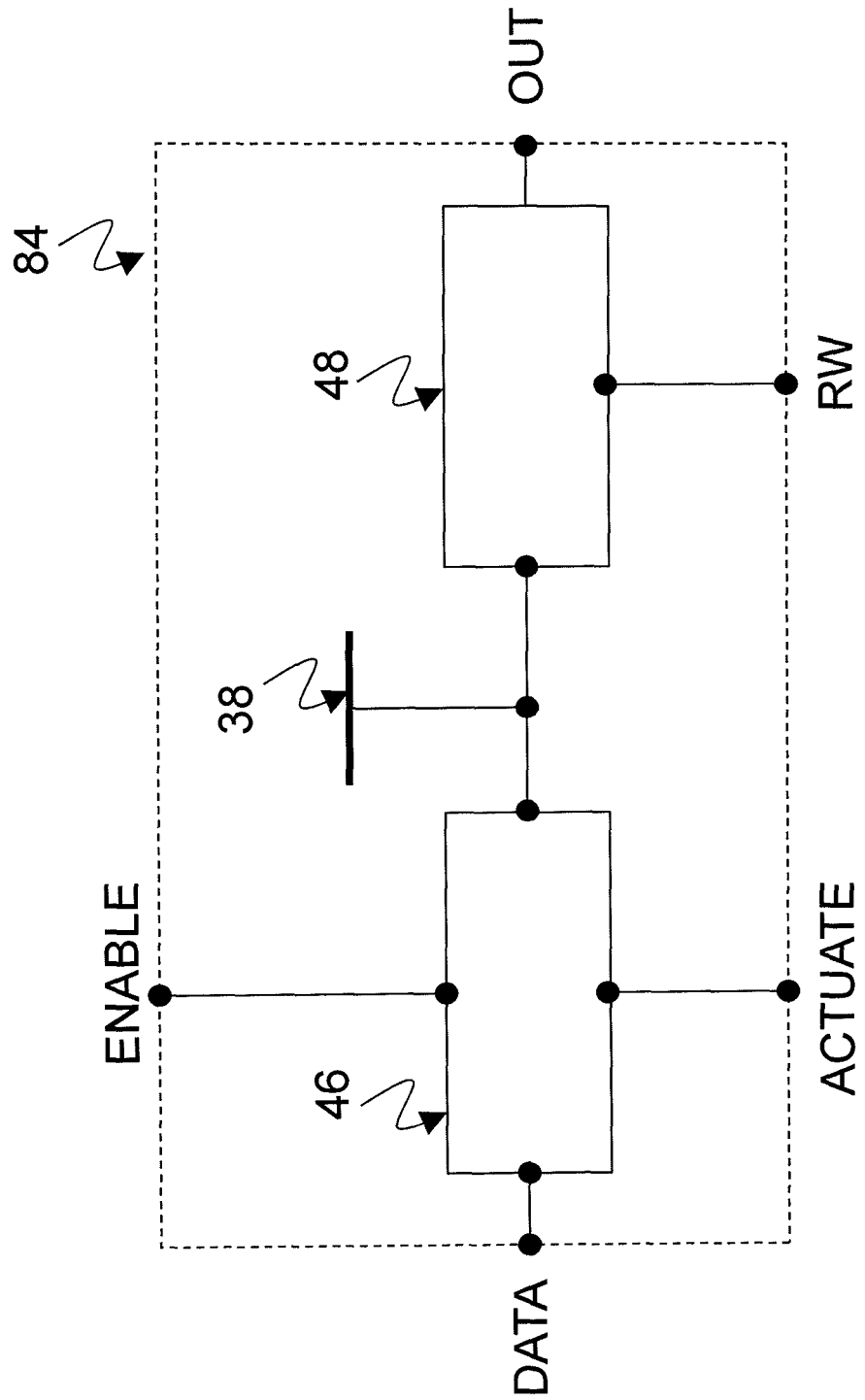
FIG. 7 shows a schematic arrangement of the array element circuit in accordance with a first embodiment of the invention.

FIG. 7 is a schematic diagram showing an example arrangement of thin film electronics 74 in the array element circuit 84. The array element circuit 84 may contain an actuation circuit 46, having inputs ENABLE, DATA and ACTUATE, and an output which is connected to an element electrode 38. The array element circuit may also contain a droplet sensing circuit 48, which may be in electrical communication with the element electrode 38. Typically the read-out of the droplet sensing circuit 48 may be controlled by one or more addressing lines (e.g. RW) that may be common to elements in the same row of the array, and may also have one or more outputs, e.g. OUT, which may be common to all elements in the same column of the array.

The array element circuit 84 may typically perform the functions of:

(i) Selectively actuating the element electrode 38 by supplying a voltage to it. Accordingly any liquid droplet 4 present at the array element may be actuated or de-actuated by the electro-wetting effect.

(ii) Sensing the presence or absence of a liquid droplet 4 at the location of the array element. The means of sensing may be capacitive, optical, thermal or some other means. Commonly capacitive sensing of the liquid droplet 4 is found to be convenient to implement.

Exemplary designs of array element circuits 84 that may be used are given in U.S. Pat. No. 8,653,832 referenced in the background art section, and commonly assigned UK application GB1500261.1. These include descriptions of how the droplet may be actuated (by means of electro-wetting) and how the droplet may be sensed by capacitive means. Typically, capacitive sensing may be analogue and may be performed simultaneously, or near simultaneously, at every element in the array. By processing the returned information from such a capacitive sensor (for example in the application software 52 of the reader 40), it is possible to determine in real-time, or almost real-time the position, size, centroid and perimeter of each liquid droplet 4 present in the array.

According to the operation of the first embodiment, the AM-EWOD device 41 is used to perform a chemical or bio-chemical test (assay). In general, therefore, an aspect of the invention is a method of determining the output of an assay in a microfluidic device. In exemplary embodiment the assay may be for testing the concentration of a substance in a droplet of sample. The sample may be comprised of any material that the user wishes to test. It may for example comprise of one of water, purified or specially treated water, a physiologic substance (e.g. blood, urine, sweat, tears or any other bodily fluid), a synthesised chemical (for example a drug, medicine, foodstuff or supplement) or of any other substance which the end user may wish to test for (assay). In exemplary embodiments, the assay output determining method includes the steps of: dispensing a sample droplet onto a first portion of an electrode array of the microfluidic device; dispensing a reagent droplet onto a second portion of the electrode array of the microfluidic device; controlling actuation voltages applied to the electrode array of the microfluidic device to mix the sample droplet and the reagent droplet into a product droplet; sensing a dynamic property of the product droplet; and determining an assay of the sample droplet based on the sensed dynamic property. The dynamic property of the product droplet may be a physical property of the product droplet that influences a transport property of the product droplet on the electrode array of the microfluidic device.

Figure 8:
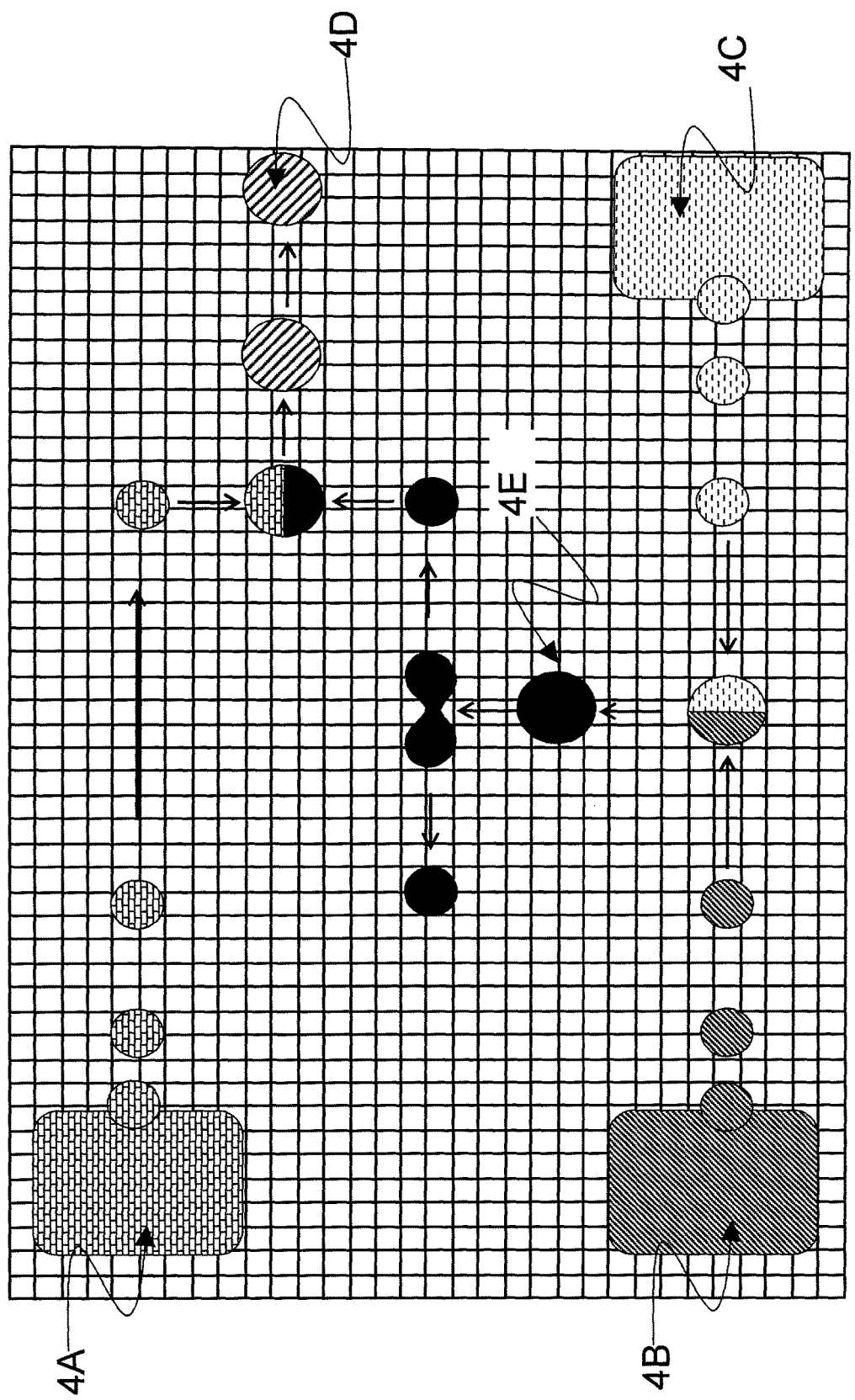
FIG. 8 shows an exemplary assay protocol for droplet operations performed on the exemplary AM-EWOD device of FIG. 3.

An exemplary assay protocol may be as shown in FIG. 8. The AM-EWOD device 41 may be used to manipulate liquid droplets of input sample and reagents (for example 4A, 4B and 4C). Example droplet operations may include some or all of the following:

Dispensing of droplets from larger "reservoirs" of fluid;
Moving of droplets to different locations in the array;
The coalescing and mixing of droplets. The mixing may be by diffusion or by active agitation of the droplets;
The splitting of droplets into two or more daughter droplets, of substantially equal or unequal sizes;
The heating, cooling or maintenance at a constant temperature of droplets; and
The manipulation of a solid phase, for example beads or cells. This may be done by external means, for example the application of a magnetic field, by optical tweezers.

The sequence shown in FIG. 8 includes the steps of:

Dispensing from reservoirs droplets of a sample droplet 4B, and reagent droplets 4C and 4A onto respective portions of the electrode array;
Mixing the daughter droplet of sample 4B with a droplet of reagent 4C to create an intermediate product droplet 4E;
Splitting intermediate product droplet 4E into two daughter droplets; and
Mixing a daughter droplet produced by the splitting of intermediate product droplet 4E with reagent 4A to create a droplet of a final product droplet 4D.

It will be understood that the sequence shown in FIG. 8 is an exemplary protocol for the purposes of illustration and explanation. Any arbitrary protocol may be defined and programmed according to the requirements of the assay and may involve a large number of droplets and droplet operations in order to create one or more final product droplets 4D.

For each step of the assay, the positions and sizes of the individual droplets may be sensed by means of the droplet sensor function of the AM-EWOD device 41 as previously described.

According to the operation of the first embodiment, the assay protocol may be such that the final mix operation (of droplets of 4A and 4E) produces a product droplet 4D. The chemistry of the assay may be chosen such that the product droplet 4D has a dynamic property that depends in some way on the result of the assay being performed.

In general, a dynamic property may be defined to be any physical property of a droplet (for example relating to its content or constitution) that influences in some way its transport properties on the AM-EWOD device 41.

According to a first embodiment the relevant dynamic property of the product droplet 4D may be whether the product droplet 4D can be moved, or not, on the AM-EWOD device 41. Specifically, the dynamic property of the product droplet 4 may cause it to be classified as being in either a movable or immovable state. Specifically these states are defined as:

Movable state: The droplet 4D is capable of being moved by the electro-wetting force, in accordance with the droplet actuation operation of the device; or Non-movable state: the droplet 4D is incapable of being moved by the electro-wetting force, i.e. the droplet is unable to be moved by the actuation operation of the device.

Figure 9:
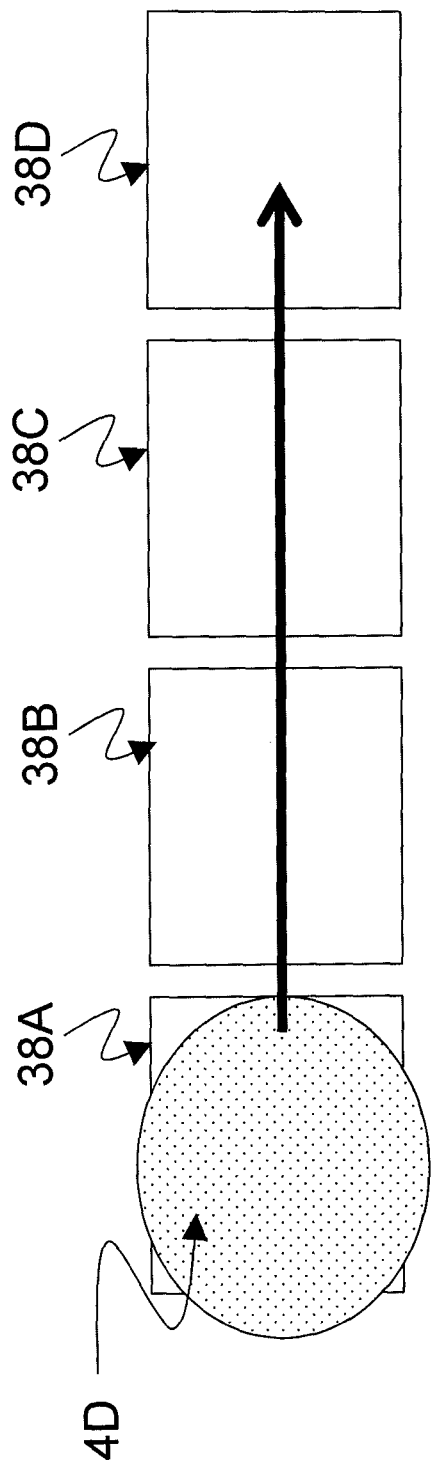
FIG. 9 shows a part of the AM-EWOD device of FIG. 3, and an exemplary method to measure whether a droplet movement operation can be implemented, according to a first embodiment of the invention.

According to whether the product droplet 4D is in a movable state or non-movable state as defined above, the result of the assay may be sensed. The assay determining method may include actuating a portion of the electrode array associated with the product droplet, and then sensing whether the product droplet is in a moveable or non-moveable state. This may be done, for example, by applying an actuation sequence (i.e. a sequence of electro-wetting voltages) to the AM-EWOD device 41 that would move the droplet. For example, as shown in FIG. 9, an actuation sequence could be applied that successively actuates element electrodes 38A, 38B, 38C and 38D with the intention of moving the product droplet 4D from element electrode 38A to element electrode 38D. According to whether the move operation is successfully effected or not, it may be determined whether the droplet 4D is in a movable state or non-movable state as defined above.

The sensing of whether the move operation is successful or not may optionally be performed by a sensor that is part of the assay measurement system. The droplet sensor function for the system may be incorporated into each array element of the AM-EWOD device 41. In particular, a sensor may be an integrated sensor that is integrated into array element circuitry of the electrode array. Alternatively, the system sensor for the move operation may be carried out by an external sensor, for example by observation by an external CCD camera. More generally, integrated and/or external sensors may be employed to perform any of the senor functions described herein.

The chemistry change effected in the product droplet 4D may be anything that causes a change in one or more droplet dynamic properties that is sufficient to prevent movement. A droplet dynamic property, sufficient to cause the product droplet 4D to be transformed into an immovable state may, for example, be any of the following:

A change in phase of the product droplet 4D from a liquid to a solid phase.
A change in phase of the product droplet 4D from a liquid to a gel.
A change in phase of the product droplet 4D from a liquid to a gas.
The formation of a solid precipitate within the product droplet 4D, which may be such that the droplet can no longer be moved.
A change of the viscosity of the product droplet 4D to a high value such that this droplet can no longer be moved.
A change of the chemical constitution of the product droplet 4D such that it transitions from a substantially polar constitution to a substantially non-polar constitution, such as can no longer be manipulated by the electro-wetting force.
The creation of a chemical or bio-chemical species within the product droplet 4D that changes the constitution of either or both of the hydrophobic coatings (16 and 26) such that they are in a permanent or semi-permanent hydrophilic state. This will have the effect of preventing droplet movement away from that location since the droplet will no longer be preferentially attracted to an actuated neighboring array element, since the initial position is sufficiently hydrophilic. Examples of means whereby the hydrophobic properties of the surface(s) may be so altered may include the chemical degradation or etching of the hydrophobic coating material or the fouling of the surface, for example by means of proteins in the product droplet 4D.

Specific examples of particular assays which may result in the inducement one or more of these effects in the product droplet are described in later embodiments of the invention.

The chemistry change effected in the product droplet 4D to cause it to be transformed into an immovable state may happen instantaneously or nearly instantaneously. Alternatively, the change may happen over a longer period time, and optionally there may be a programmed delay in the assay sequence between forming the intermediate product droplet and mixing the intermediate product droplet with the second reagent droplet (mixing of droplets 4E and 4A), and the attempt to move the product droplet 4D and thus determine the result of the assay. This programmed delay may be of a length of time in the range of a few milliseconds to hours or tens of hours according to the chemistry of the assay. During the programmed delay, the product droplet 4D may be maintained in either an actuated or a non-actuated state. During the programmed delay, the droplet temperature may optionally be uncontrolled, may be maintained constant, may be varied or may be thermally cycled according to the requirements of the assay.

The assay may be arranged such that a positive result (for example the presence of a particular target chemical or bio-chemical species in the sample droplet 4A that the assay is designed to detect) results in the product droplet 4D being in a non-movable state, whilst a negative result (the absence of the target species from the sample droplet 4A) results in the product droplet 4D being in a movable state.

Alternatively the assay may be arranged such that a positive result results in the product droplet 4D being in a movable state, whilst a negative result results in the product droplet 4D being in a non-movable state.

An advantage of the invention is that the result of the assay may be determined directly from a dynamic property of the product droplet, specifically whether the product droplet 4D can be moved at the conclusion of the assay. The invention thus provides for an integrated means of detecting the result of an assay that is label free and does not require the use of optical techniques to interrogate the droplet.

A further advantage of the invention is that the detection of assays involving a viscosity change, phase change, gel formation, precipitation or other related changes may be performed by electronic means in a microfluidic device. In macroscopic (e.g. test tube) formats, determining the result of such an assay (e.g. the formation of a gel or precipitate) may be subjective and, for example, subject to the decision of a trained technician or operator of whether a gel or precipitate, or the like has formed. This subjectivity may reduce the measurement sensitivity of the assay and also necessitates the assay to be performed by trained personnel who are competent to judge the result of the assay. By performing and sensing the assay by automated means in a microfluidic device, this element of subjectivity is removed. The assay may therefore be more sensitive. Furthermore, it may be possible for a measurement using the microfluidic device to be performed by relatively unskilled operators.

A further advantage is that the assay is performed in a microfluidic format using only small volumes of samples and reagents. This may be advantageous for reducing the time required to perform the assay, since the time required for a gel to form, precipitate to form or phase change to occur, for example, may be less for microfluidic quantities of materials taking place in the reaction. This advantage may be further aided by the rapid mixing capability of the AM-EWOD device 41 whereby droplets may be rapidly mixed by agitation.

A further advantage is that by performing the assay in a microfluidic format, the sensitivity of the assay may be improved. This may be, for example, because the results of the assay are less subject to sample-to-sample variability or stochastic variations.

A further advantage of the invention is that by performing assays in a digital microfluidic format, the volumes of the samples and reagents used may be made very small, for example microliters, nanolitres or picolitres. This is advantageous for reducing cost if either the sample or reagents are expensive, scarce or precious.

Furthermore, all the above advantages may be achieved by adding minimal additional complexity to the cartridge 44, reader 40 and AM-EWOD device 41. No external detection optics are required in the reader 40, and the results of the assay may be determined by electronic means as defined by a computer program running the application software. This has the advantage of enabling the assay to be performed in a simple and easy to use system. For example, compared to using an optical means of detection in an AM-EWOD device 41, the system is considerably simplified since no illumination or detection optics are required in the reader 40 and optical considerations do not need to be considered in the design of the cartridge 44. This results in a smaller, simpler and lower cost cartridge 44 and reader 40, and a system that is very easy to use for a non-specialist operator.

A second embodiment of the invention is comparable to the first embodiment except that a different dynamic property of the product droplet 4D is used to determine the result of the assay. According to a second embodiment, the assay result determining method may include actuating a portion of the electrode array associated with the product droplet, and the dynamic property criteria is whether the product droplet 4D may be split into two daughter droplets or not by actuation of the electrode portion. If the product droplet 4D may be split into two daughter droplets, for example by application of an example droplet splitting sequence, the product droplet is defined as being in a split-able state. If the product droplet 4D cannot be split into two daughter droplets, it is defined as being in a non-split-able state.

Figure 10:
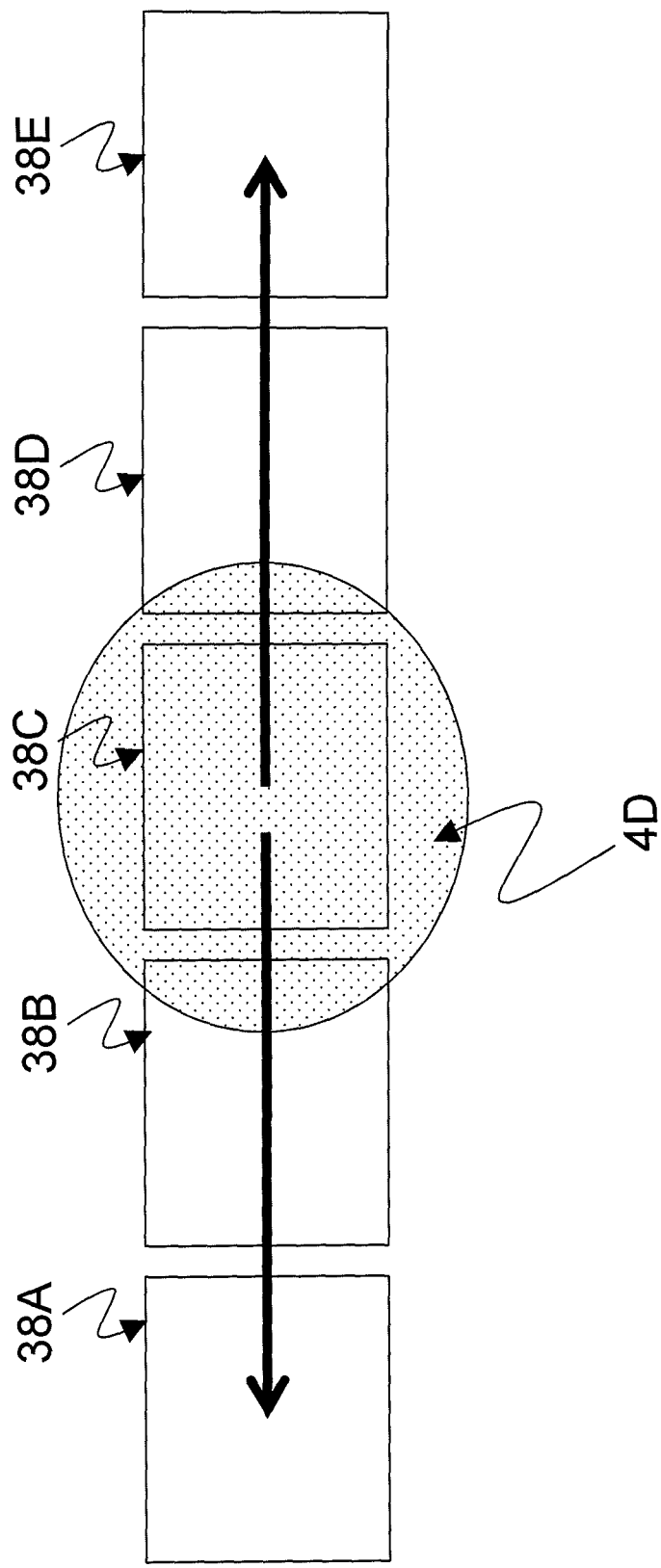
FIG. 10 shows a part of the AM-EWOD device of FIG. 3, and an exemplary method to measure whether a droplet splitting operation can be implemented, according to a second embodiment of the invention.

This concept is illustrated in FIG. 10. According to the operation of the device according to this embodiment, an actuation pattern is applied to the element electrodes that would generally be sufficient to split the product droplet 4D (shown initially located at element electrode 38C) into two daughter droplets, to be located at element electrodes 38A and 38E. The sensor capability of the AM-EWOD device 41 may then be used to determine whether or not the splitting operation has successfully occurred. Accordingly, the result of the assay, i.e. whether the product droplet 4D is in a split-able or non-split-able state, may thus be determined. An advantage of the second embodiment is that a splitting test may be more sensitive than a movement test to whether a change in the properties of the product droplet 4D has occurred in accordance with the result of the assay. This method may thus be capable of detecting smaller quantities of the target substance in the sample droplet.

The method of determining the result of the assay according to operation according to the first or second embodiments may be termed digital, since the result of the assay is a "Yes/No" test of a dynamic property of the product droplet 4D.

Figure 11:
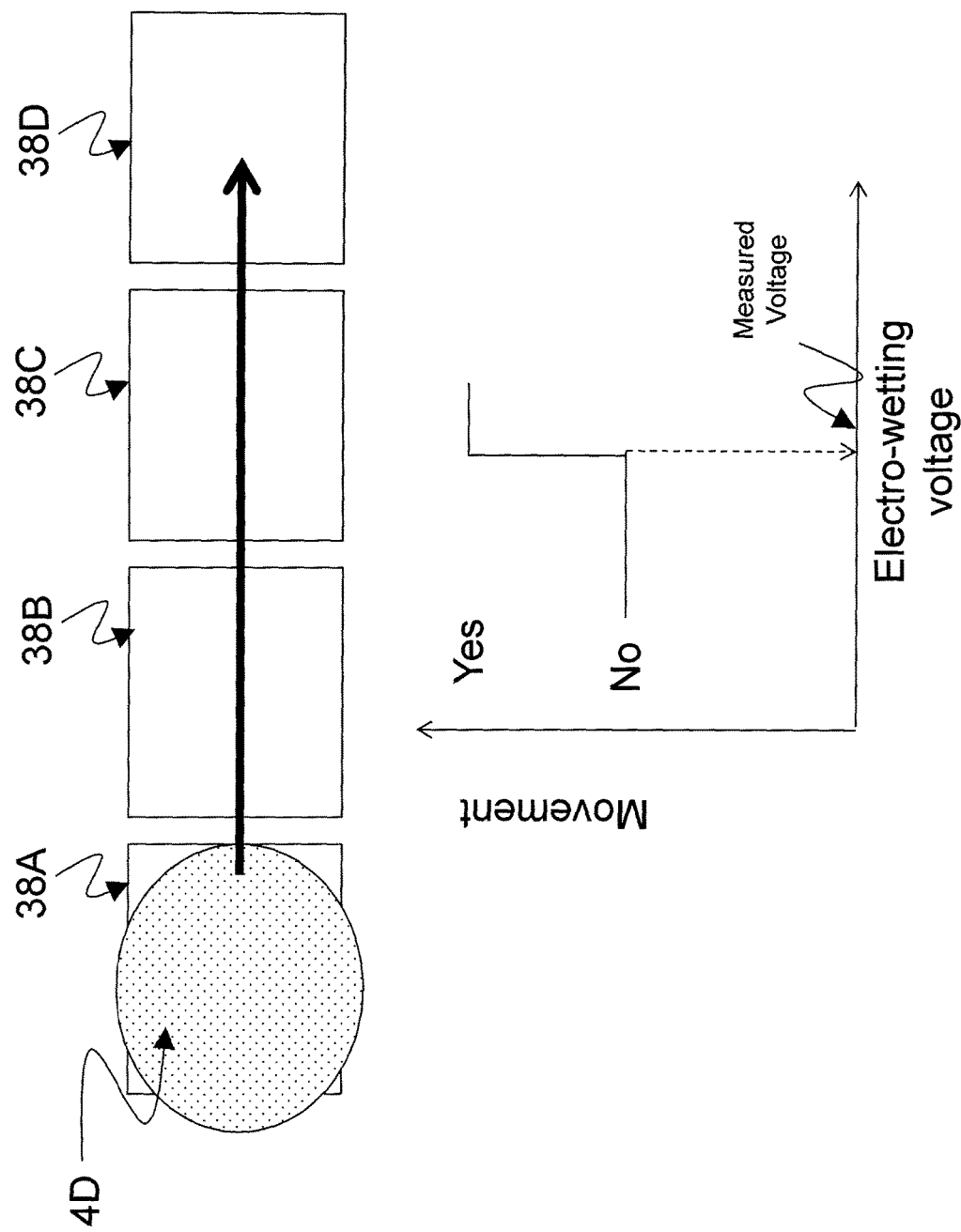
FIG. 11 shows a part of the AM-EWOD device of FIG. 3, and an exemplary method to measure whether a droplet movement operation can be implemented at different electro-wetting voltages, according to a third embodiment of the invention.

A third embodiment of the invention is comparable to the first or second embodiments except that a different method is used to determine whether the product droplet 4D is in movable or non-movable state, shown schematically in FIG. 11. According to this embodiment, an attempt is made to move the product droplet 4D with the electro-wetting voltage set to some low value, for example half of the usual value. If the attempt to move the product droplet 4D fails, (i.e. the product droplet is in a non-movable state at this electro-wetting voltage), the electro-wetting voltage is increased (typically, for example by 5%) and the process is repeated in multiple steps until the droplet is in a moveable state. The measured quantity according to this means of operation is the minimum electro-wetting voltage required to effect a movement of the product droplet 4D, i.e. the minimum electro-wetting voltage for which the product droplet 4D is rendered into a movable state from a non-moveable state. An advantage of the third embodiment is that it gives a quantified number (a measurement voltage) and thus may be more sensitive than the first embodiment to the result of the assay. As a result, it may be possible to detect smaller concentrations of the target substance in the sample droplet 4B than may be detected by the method of the first embodiment. In a variant of the third embodiment, the dynamic property of the product droplet being sensed may instead be the minimum electro-wetting voltage required to split the product droplet 4D into two daughter droplets, i.e. the minimum electro-wetting voltage required for the product droplet 4D to render the droplet into a split-able state from a non-split-able state.

Figure 12:
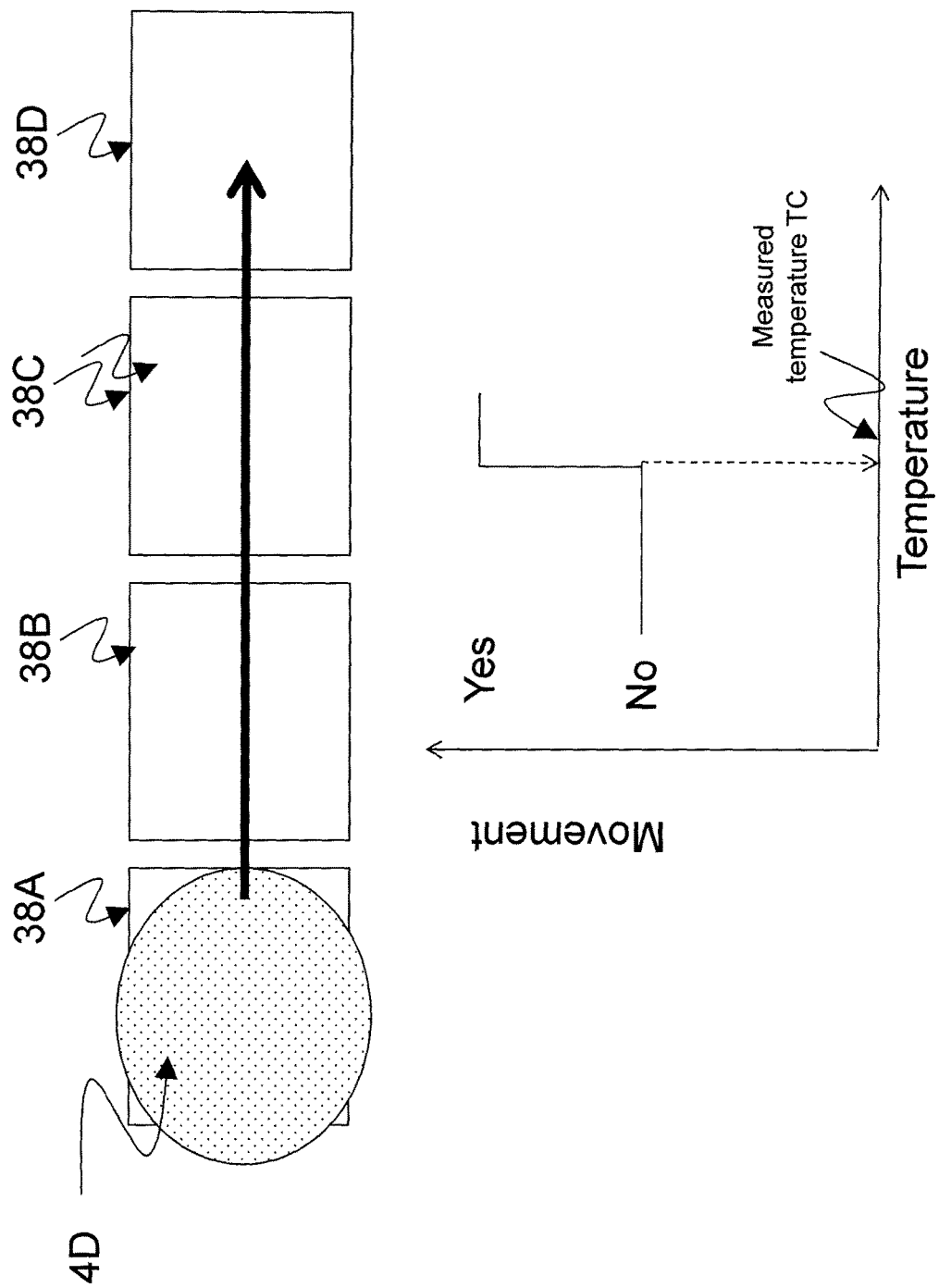
FIG. 12 shows a part of the AM-EWOD device of FIG. 3, and an exemplary method to measure whether a droplet movement operation can be implemented at different temperatures, according to a fourth embodiment of the invention.

A fourth embodiment of the invention is comparable to the first or second embodiments except that a different method is used to quantify a dynamic property of the product droplet 4D. This method is shown schematically in FIG. 12. According to the fourth embodiment, the temperature is set to some low value (for example 20° C.), and an attempt is made to move the product droplet 4D, i.e. to determine whether the product droplet 4D is in a movable or non-movable state. If this attempt to move the product droplet 4D fails, the temperature is increased by some increment (for example by 1° C.) and the process is repeated in multiple steps until the droplet is in a moveable state. The measured quantity according to this means of operation is the minimum temperature required to effect a movement operation of the product droplet 4D, i.e. the minimum temperature required for the product droplet 4D to be rendered into a movable state from a non-moveable state. This embodiment may be particularly advantageous where the operation of the assay causes the product droplet 4D to undergo a change in state, for example to a solid or gel state. The product droplet may revert to a liquid (and movable state) at some critical temperature. The measurement of this critical temperature may, for example, be a function of the concentration of the target substance in the sample droplet 4B. Measurement of the critical temperature may therefore give information regarding the concentration of a target species in the original sample droplet.

Such a means of detecting the result of an assay as described by this embodiment may be advantageous for some assays as it is particularly sensitive and may give a particularly accurate result.

A fourth embodiment has been described with regard to determining a dynamic property of the product droplet 4D according to whether it is in a movable or non-movable state. Equally, it will be appreciated that the principles of the fourth embodiment could be combined with the second embodiment, i.e. a measured dynamic property of the product droplet 4D may be whether the product droplet 4D is in a split-able or non-split-able state as previously described. Such embodiment includes determining a minimum temperature to render the product droplet into a split-able state from a non-split-able state.

The method of determining the result of the assay in operation according to the third or fourth embodiments may be termed multi-digital, since the result of the assay is a "Yes/No" test of a dynamic property of the product droplet 4D (e.g. movable/non-movable or split-able/non-split-able), but the test is performed under a number of different conditions (either with different applied voltages or at different temperatures).

Figure 13:
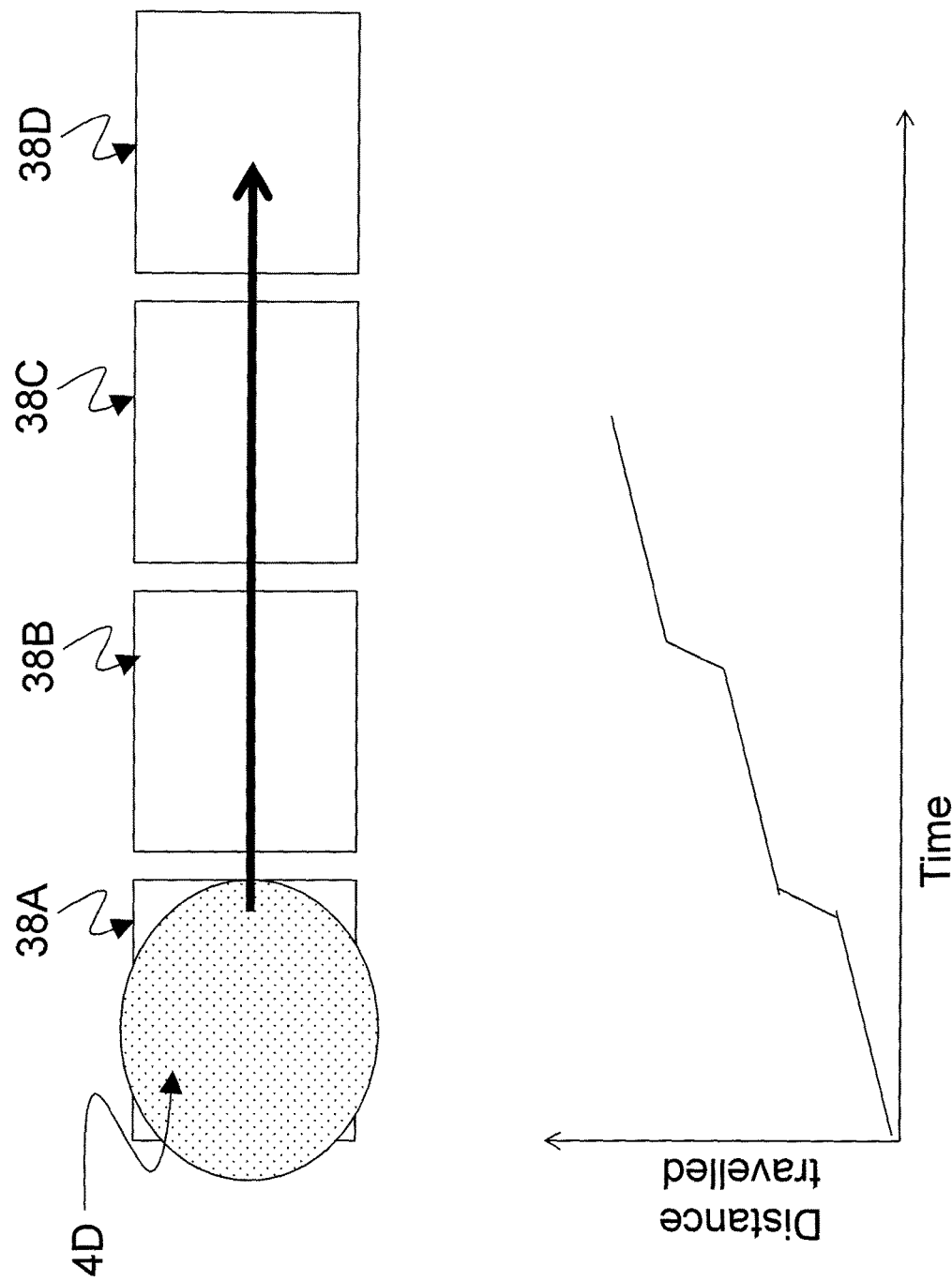
FIG. 13 shows a part of the AM-EWOD device of FIG. 3, and an exemplary method to measure the maximum speed of droplet movement, according to a fifth embodiment of the invention.

A fifth embodiment of the invention is comparable to the first embodiment except that a different method is used to measure a dynamic property of the product droplet 4D. In operation of the device according to this embodiment, the assay determining method may include actuating a portion of the electrode array associated with the product droplet, and the maximum average speed of movement of the product droplet 4D is measured. FIG. 13 is a schematic diagram showing exemplary operation according to this embodiment. The product droplet is moved from element 38A to 38D, and the minimum time taken to traverse this distance is measured.

Such a droplet speed measurement may be done in a number of ways. For example, a pattern of voltages to move the droplet from element electrode 38A to element electrode 38D may be applied. The move pattern may for example actuate elements 38A, 38B, 38C and 38D in turn and be programmed such as to effect movement at a certain rate (e.g. each element is actuated for a certain defined time period). According to the constitution of the product droplet 4D, movement from 38A to 38D may or may not be effected by the move pattern when written at this rate to the elements of the array. If it is the case that the movement is not effected, the rate may be slowed down and the process repeated. This method may thus be used to determine the maximum speed of movement of the product droplet, from the minimum time in which the movement from 38A to 38D can be undertaken. As previously, the determination of whether a programmed move operation has actually occurred may be done by using the integrated sensing function of the AM-EWOD device 41, or alternatively by external means (e.g. using a CCD camera).

In a variant of the fifth embodiment, the actuation function and sensor function of the AM-EWOD device 41 may be configured to operate in a feedback mode in order to implement a move operation. For example, an actuation pattern may be applied to move the product droplet 4D from its starting position (38A) to the neighboring array element 38B. This actuation pattern may involve, for example, de-actuating 38A and actuating 38B, such that the product droplet 4D moves from element electrode 38A to element electrode 38B. During the move operation the position of the droplet may be determined using the integrated sensor function at each of element electrodes 38A and 38B. Accordingly it may be determined when the droplet has reached element electrode 38B according to some criteria (for example by a measurement of the centroid position of the droplet, or alternatively by measurement of the position of the edges of the droplet). At this point element 38B may be de-actuated and element 38C actuated to move the droplet on to element electrode 38C. When the sensor function detects the arrival of the product droplet 4D at element electrode 38C, this element may then be de-actuated and element 38D actuated. The operation concludes when the product droplet is detected as having arrived at element 38D, and the total time taken is measured. In this way the maximum speed of the droplet may be determined.

An additional advantage of the fifth embodiment compared to previous embodiments is that it implements an analogue method of sensing a dynamic property of the product droplet 4. By measuring the maximum speed of the product droplet, the readout of the assay result may be performed in an analogue way. This embodiment is particularly effective for quantifying assays where the resulting quantity of measurement is the viscosity of a product droplet 4, since there is typically an approximately linear relationship between maximum velocity and droplet viscosity. This method may therefore be particularly advantageous for performing assays where the viscosity of the final product droplet 4D is directly related to the concentration of the target species in the sample droplet 4B.

In a further refinement of operation according to the fifth embodiment, the integrated sensor capability may also be used to measure the size of the product droplet 4D. This may provide important calibration information for the determination of the assay based on a relation between the size and average speed of movement of the product droplet, since maximum droplet speed typically depends on droplet size as well as droplet viscosity. In this way the measured result may be compensated for any variability in the result, for example due to test-to-test variations in the size of the product droplet 4D caused, for example, by variability in the splitting operations performed as part of the assay protocol.

Figure 14:
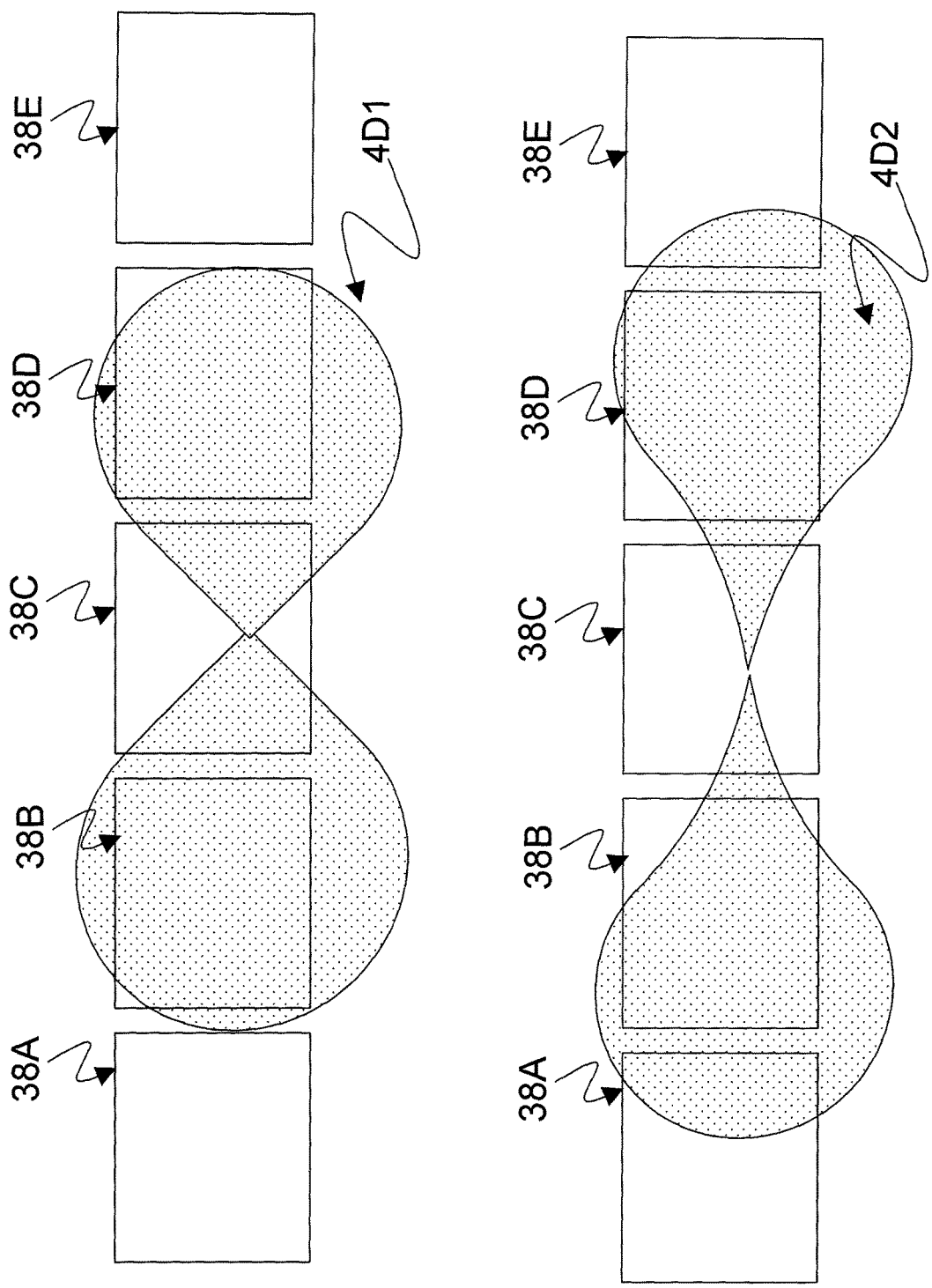
FIG. 14 shows a part of the AM-EWOD device of FIG. 3, and an exemplary method to measure the splitting characteristics of a droplet, according to a sixth embodiment of the invention.

A sixth embodiment of the invention is comparable to the first embodiment except that a different method is used to determine a dynamic property of the product droplet 4D based on the viscosity of the product droplet as being related to a measured dynamic parameter. In the operation of the device according to this embodiment, an actuation pattern appropriate to effect a split operation is applied to the product droplet 4D. The sensor function integrated in the AM-EWOD device 41 may be used to determine the approximate droplet perimeter and thus determine the time at which the product droplet 4D splits into two daughter droplets. Typically, the viscosity of a liquid droplet 4 is found to have an impact on splitting. This is shown schematically in FIG. 14. The upper part of the figure shows the typical perimeter of a low viscosity droplet 4D1 at the point where splitting occurs. The lower part of the figure shows the typical perimeter of a high viscosity droplet 4D2 at the point where splitting occurs. As is shown in FIG. 14, the higher the viscosity of the droplet the further apart the centroids of the two emergent daughter droplet products must be pulled in order to break the "neck" that forms during the splitting operation. Therefore, by means of a measurement of the distance between the centroids at the time of splitting, the droplet viscosity may be measured. Alternatively, and equivalently, the viscosity may be determined from the time required to effect the split from the time at which the voltage pattern begins to be applied. The advantages of the sixth embodiment are similar to those of the fifth embodiment, that by measuring the viscosity of the product droplet 4D the result of the assay may be determined.

A seventh embodiment of the invention is comparable to any of the previous embodiments, with the additional feature that a measured dynamic property of the product droplet 4D is also compared to a measured dynamic property of a reference droplet 4P. In such embodiment, the array determining method may include the steps of: dispensing a reference droplet onto another portion of the electrode array; sensing the dynamic property of the reference droplet; and determining the result of the assay of the sample droplet by comparing the sensed dynamic property of the product droplet to the sensed dynamic property of the reference droplet.

Figure 15:
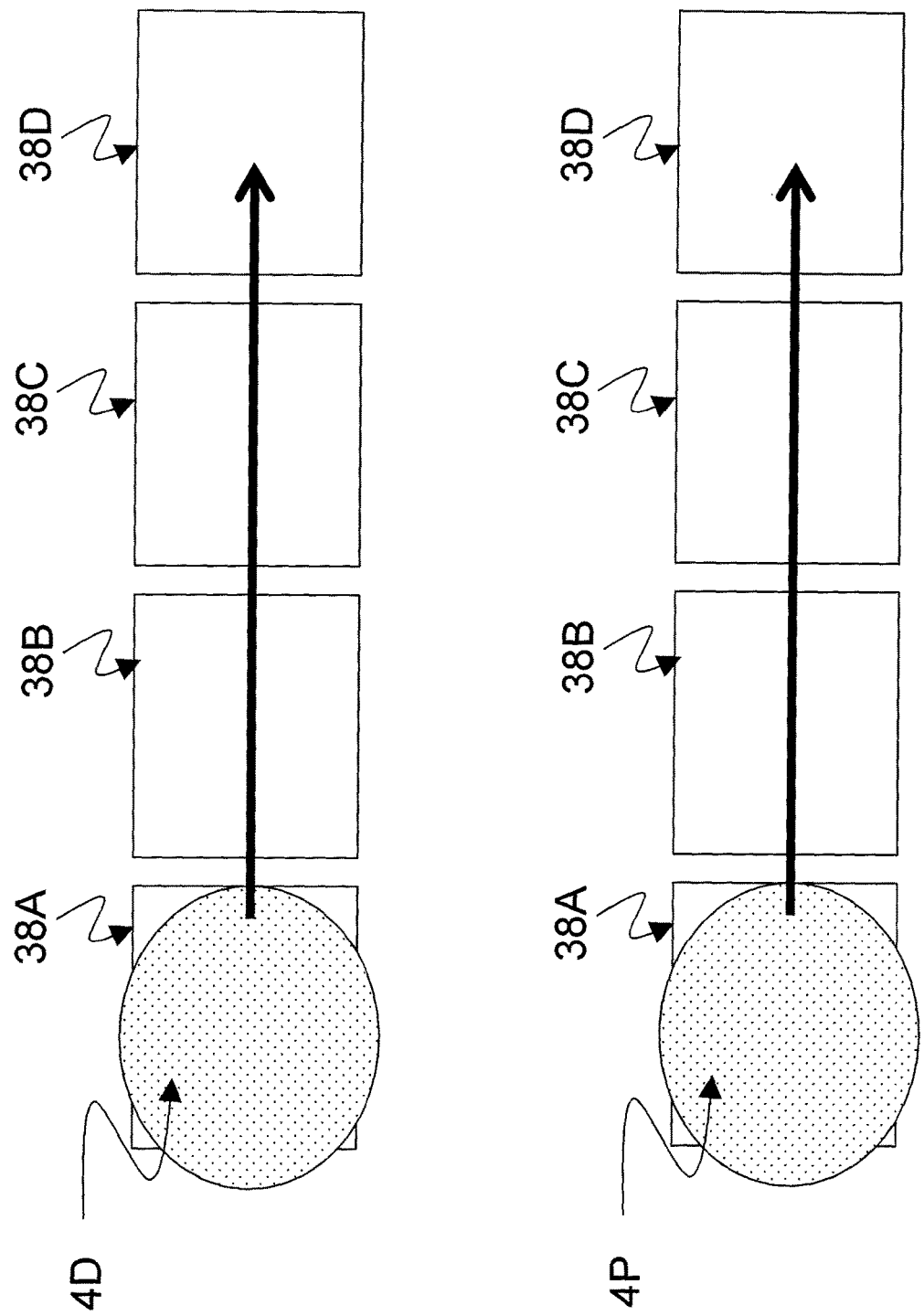
FIG. 15 shows a part of the AM-EWOD device of FIG. 3, and an exemplary method to measure the maximum movement speed of a droplet in a differential mode, according to a seventh embodiment of the invention.

The reference droplet 4P may be of a known constitution. This method therefore implements what is in effect a differential measurement of a dynamic property of the product droplet 4D. FIG. 15 shows an example implementation where the differential measurement principle of this embodiment is applied with the measurement method of the fifth embodiment. The maximum speed of the product droplet 4D may be measured as was previously described. The maximum speed of the reference droplet 4P may also be measured using the same method. The measurement result obtained from measurement of the reference droplet 4P may be used to calibrate the measurement result obtained from measurement of the product droplet 4D.

An advantage of this embodiment is that the measurement result from the reference droplet 4P may thus be used to calibrate the measurement. In this way any variability in the result due to the device-to-device variations or variations in the operating conditions may be compensated for and calibrated out in the measurement software. Examples of factors that may cause such variability include device-to-device variation in layer thicknesses (which may influence the strength of the electro-wetting force), device-to-device variations in the cell gap spacing between the top and bottom substrates, and variations in the ambient temperature, all of which may affect the measurement results obtained for both the product droplet 4D and the reference droplet 4P.

The principle of using a reference droplet as described in the seventh embodiment, has been illustrated with respect to combination with the fifth embodiment. Equally it will be clear to one of ordinary skill in the art how the principle of the seventh embodiment may also be combined with the measurement methods of any one of embodiments one to six using a reference droplet relative to any suitable dynamic property.

Figure 16:
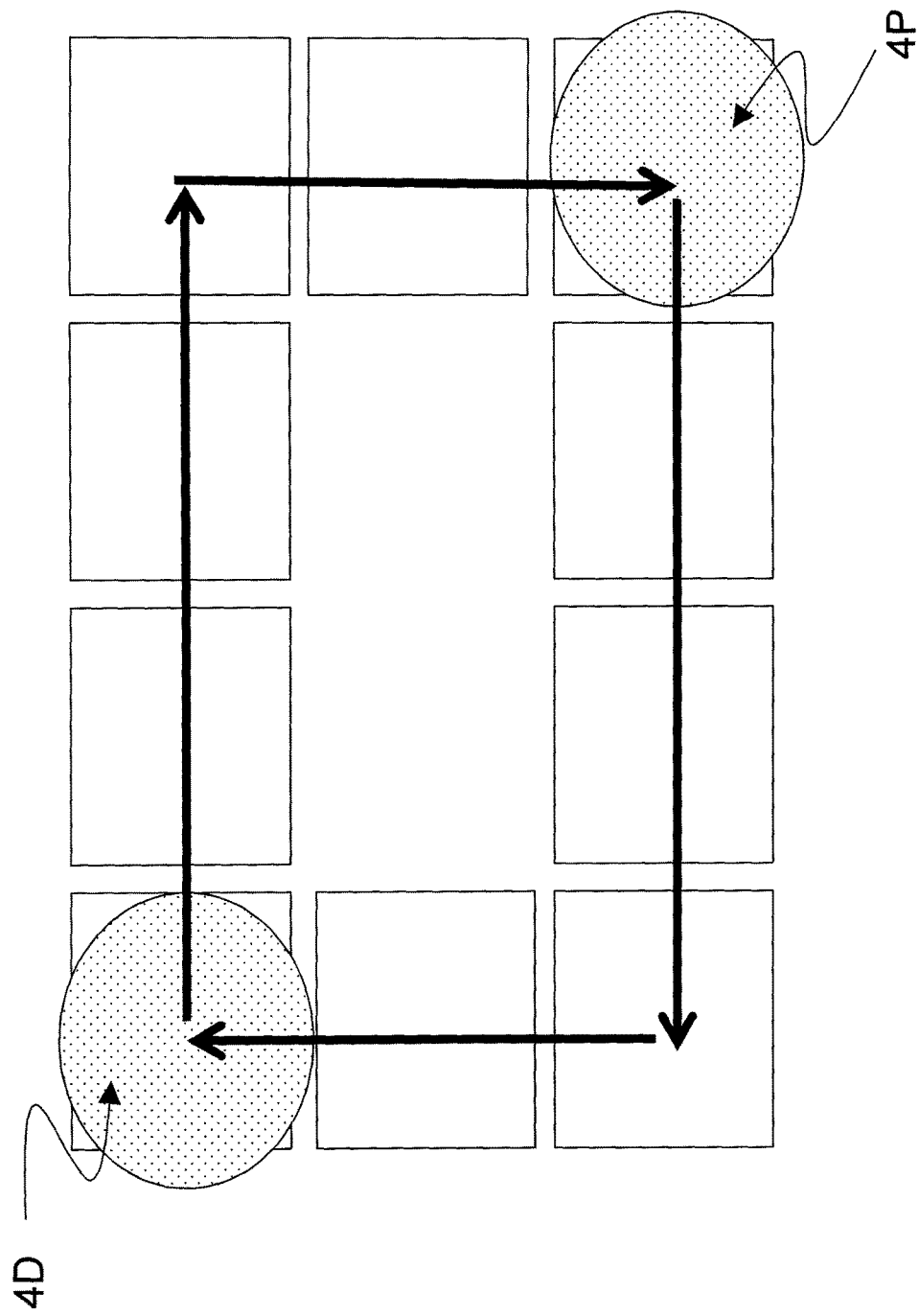
FIG. 16 shows a part of the AM-EWOD device of FIG. 3, and a further exemplary method to measure the maximum movement speed of a droplet in a differential mode, according to an eighth embodiment of the invention.

An eighth embodiment is comparable to the seventh embodiment, where the reference droplet 4P is arranged to traverse the same trajectory in the array as the product droplet 4D. The maximum speed of the product droplet 4D may be measured and compared to the maximum speed of a reference droplet 4P, in an implementation where each of the droplets traverses the same path through the array. An example implementation is shown schematically in FIG. 16. The product droplet 4D and reference droplet 4P are each arranged to traverse a rectangle of electrodes, such that in the course of the traversal each droplet follows the same path. An advantage of this embodiment is that any variations in the measured maximum speed, for example due to small variations in the thickness or quality of the hydrophobic coating in different areas of the device, are calibrated out because each of the product droplet 4D and reference droplet 4P traverses the same path.

A ninth embodiment of the invention is an extension of the seventh embodiment where multiple reference droplets (4P, 4Q, 4R, 4S) may be measured. In such embodiment, the array determining method may include the steps of: dispensing multiple reference droplets onto respective portions of the electrode array; sensing the dynamic property of the reference droplets; generating a calibration curve based on the sensed dynamic property of the reference droplets; plotting the sensed dynamic property of the product droplet on the calibration curve; and determining the assay of the sample droplet based on the plot of the dynamic property of the product droplet on the calibration curve.

Figure 17:
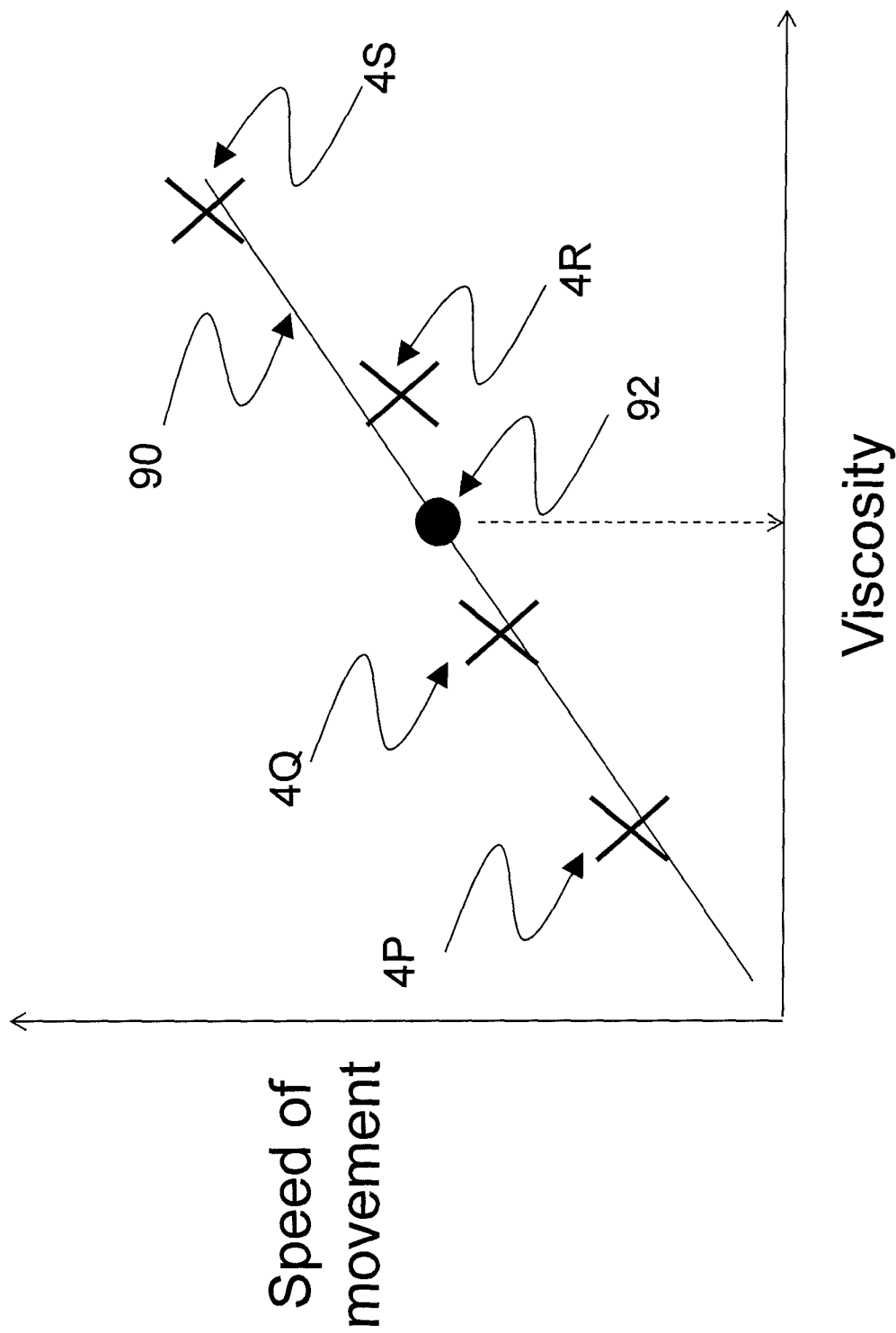
FIG. 17 is graph illustrating how droplet viscosity may be inferred from maximum droplet movement speed in a case where multiple reference droplets are also measured, according to a ninth embodiment of the invention.

An exemplary implementation of this principle is shown schematically in FIG. 17, which shows a graph of measured droplet speed versus droplet viscosity. The maximum speed of each of four reference droplets 4P, 4Q, 4R and 4S may be measured by the device. These reference droplets may each have a different and known viscosity, such that their maximum speeds and viscosities may be plotted on a graph as shown in FIG. 17. A calibration curve 90 (which may also be referred to a standard curve) may be constructed in maximum speed versus viscosity parameter space, for example by using best fit methods, as also shown in FIG. 17. Such a calibration curve 90 may have a linear dependency (as shown) or may be non-linear, as appropriate to best fit the measurement data. The maximum speed of the product droplet 4D is then measured. By plotting this measurement result 92 on the calibration curve 90, the viscosity of the measurement droplet 4D may be interpolated.

The method of the ninth embodiment has the advantages of the eighth embodiment and an additional advantage that by measuring a calibration curve 90 in this way, and plotting the measurement result 92 from the sample droplet 4D upon this calibration curve 90, very accurate measurement of the product droplet 4D viscosity may be obtained.

Figure 18:
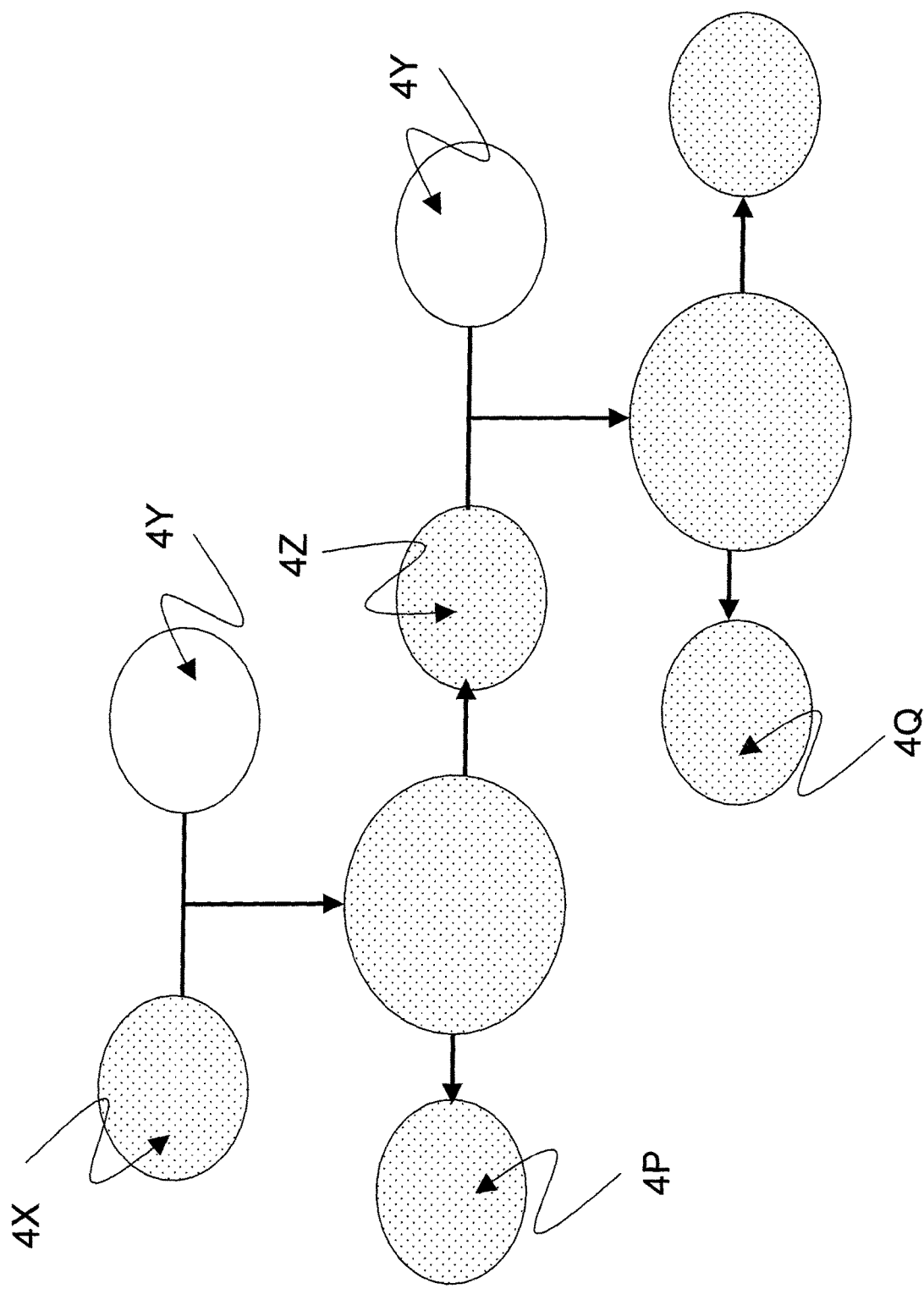
FIG. 18 shows a part of the AM-EWOD device of FIG. 3, and an exemplary protocol for generating reference droplets by serial dilution, according to an ninth embodiment of the invention.

According to a further aspect of the ninth embodiment, the reference droplets 4P, 4Q, 4R and 4S may each be input into the device separately. Alternatively, the reference droplets may be created internally within the device from a single input source. For example, reference droplets having a range of different viscosities may be created by the serial dilution of a starting reference droplet of high viscosity. For example, reference droplets could be created by performing multiple ×2 serial dilutions, by means of the protocol shown in FIG. 18. A starting reference droplet 4X may be introduced into the device. This may be diluted by a factor ×2 by mixing with a droplet of water 4Y of the same size. The product droplet may be split into two, to create reference droplet 4P and a further droplet 4Z. Droplet 4Z may then be diluted and split to create reference droplet 4Q and so on. Such a method of generating reference droplets may be particularly advantageous since it exploits the multiplexing capabilities of the AM-EWOD device 41, and reduces the number of fluid inputs required. An arbitrary number of reference droplets may be created from a single starting reference droplet 4X by such a serial dilution process, and the capability of the device to multiply dilution factors means allow the reference droplets to cover a range of several orders of magnitude in concentration.

The ninth embodiment has been illustrated above with regard to the construction of a viscosity versus maximum speed calibration curve. Other calibration curves may also be constructed, in two or more dimensions and in accordance with the measurement parameter being used to quantify a dynamic property of the product droplet 4D and thus determine the result of the assay. Examples of other calibration curves that may be constructed include, but are not limited to:

maximum speed versus droplet viscosity for different droplet sizes,
 minimum voltage required to move or to split for different reference droplet viscosities, and
 distance between the daughter droplet centroids to complete a split operation for reference droplets of different viscosities.

The choice of calibration curve parameters and data values may be made in accordance with the dynamic property of the product droplet 4D being measured and the expected range of the dynamic property of the product droplet being measured. The number, sizes and constitution of the reference droplets may be controlled (by fluid operations such as splitting, dilution, heating) to have a range of properties as is appropriate to provide a good reference to the expected range of the measurement parameters of the product droplet 4D. For example, if in a typical assay, the product droplet 4D may be expected to have a viscosity of between 3 and 10 (in arbitrary units) according to the result of the assay, the reference droplets may be arranged to have viscosities 2,4,6,8,10 and 12 in the same arbitrary units.

Embodiments 1-9 of the invention have described methods for determining a dynamic property of a product droplet 4D, which may then it turn be used to determine the result of an assay. It will be furthermore apparent to one of ordinary skill in the art how multiple of these methods may be combined, for example by sensing multiple dynamic properties of the product droplet 4D as part of the assay protocol.

Embodiments 1-9 of the invention have been illustrated with exemplary arrangement where the typical size of sample, reagent and product droplets is similar to the size of the element electrodes. This is not required to be the case in general, and implementations are also possible whereby the diameter of the liquid droplets may be twice, three times, four times or many times larger than the width of the element electrode. In certain cases there may be advantages in operation where the droplet diameter exceeds the element electrode width. For example, with larger droplets it may be possible for the droplet sizes to be measured more accurately (as measured by the droplet sensor capability), and similarly it may be possible to determine the centroid and perimeter of droplets more accurately when they encompass multiple element electrodes 38 within the array.

The following embodiments illustrate example assays, which the methods of one or more of embodiments 1-9 may be used to measure the result of the assay. In these embodiments a dynamic property of the product droplet 4D is measured, and this information is used to determine the result of the assay. The assay protocols, chemistries and condition as described in the following embodiments should be regarded as exemplary and are not intended to limit the scope of the invention in any way.

Figure 19:
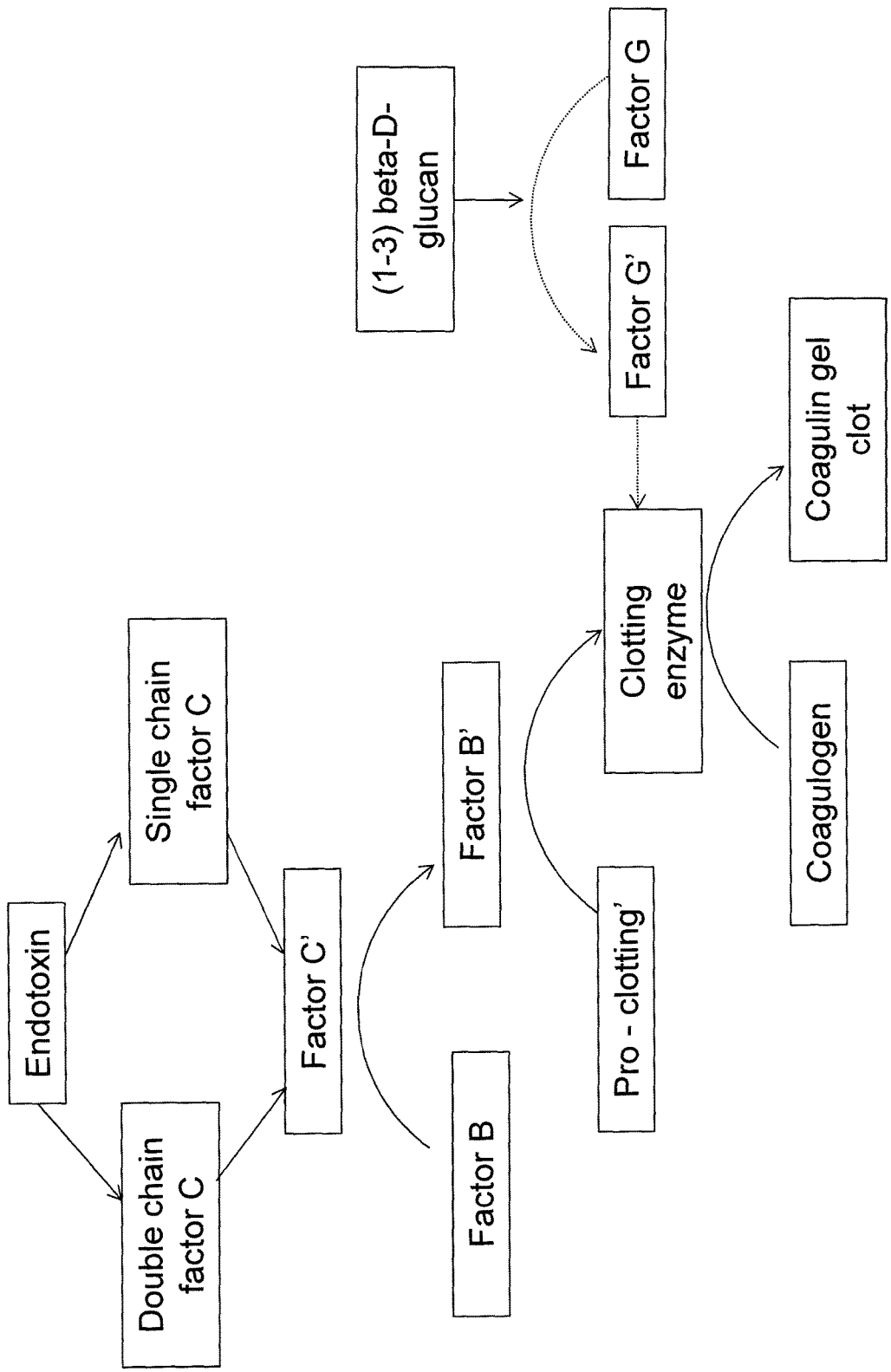
FIG. 19 shows a flow diagram of the LAL reaction pathway.

A tenth embodiment of the invention uses the device and methods of any of the previous embodiments in an assay to determine the presence or quantity of bacterial endotoxin in a sample of input material. The assay may be based on the amoebocyte lysate (LAL) component of horseshoe crab. The reaction pathway is shown schematically in FIG. 19. The assay chemistry and methods of performing the assay may be of standard means, for example as described in U.S. Pat. No. 4,495,294 and other prior art references, referenced in the background section. Optionally, and preferably, the assay chemistry may be arranged so that the LAL reagent is specifically designed so as to exclude the influence of (1,3)-beta-D-glucan on the assay test result. This may be done using well known methods in accordance with the references cited in the background section.

As further described below, therefore, an aspect of the invention is a method of performing an amoebocyte lysate (LAL)-based assay in a microfluidic device. In exemplary embodiments, the LAL-based assay method may include the steps of: dispensing a sample droplet onto a first portion of an electrode array of the microfluidic device; dispensing an LAL reagent droplet onto a second portion of the electrode array of the microfluidic device; controlling actuation voltages applied to the electrode array of the microfluidic device to mix the sample droplet and the LAL reagent droplet into a product droplet; sensing a dynamic property of the product droplet; and determining a result of the assay in the sample droplet based on the sensed dynamic property.

The bacterial endotoxin assay may be performed using a microfluidic cartridge 44 and reader 40 as previously described and shown in FIG. 2. Fluids input into the cartridge 44 include the sample material under test and LAL reagent and optionally may also include anendotoxin standard material. In the description that follows this is taken to be Controlled Standard Endotoxin (CSE), but may alternatively be Reference Standard Endotoxin (RSE) or any other suitable endotoxin standard and may also optionally be diluted in diluent water.

The fluids input into the device may be converted into droplet format by standard means and transported to the array of the AM-EWOD device 41. A controller, such as control electronics 50 executing the code 52, may control actuation voltages applied to the electrode array of the microfluidic device to perform the various droplet manipulation operation, and to determine the result of the assay based on sensed dynamic properties as described above.

Figure 20:
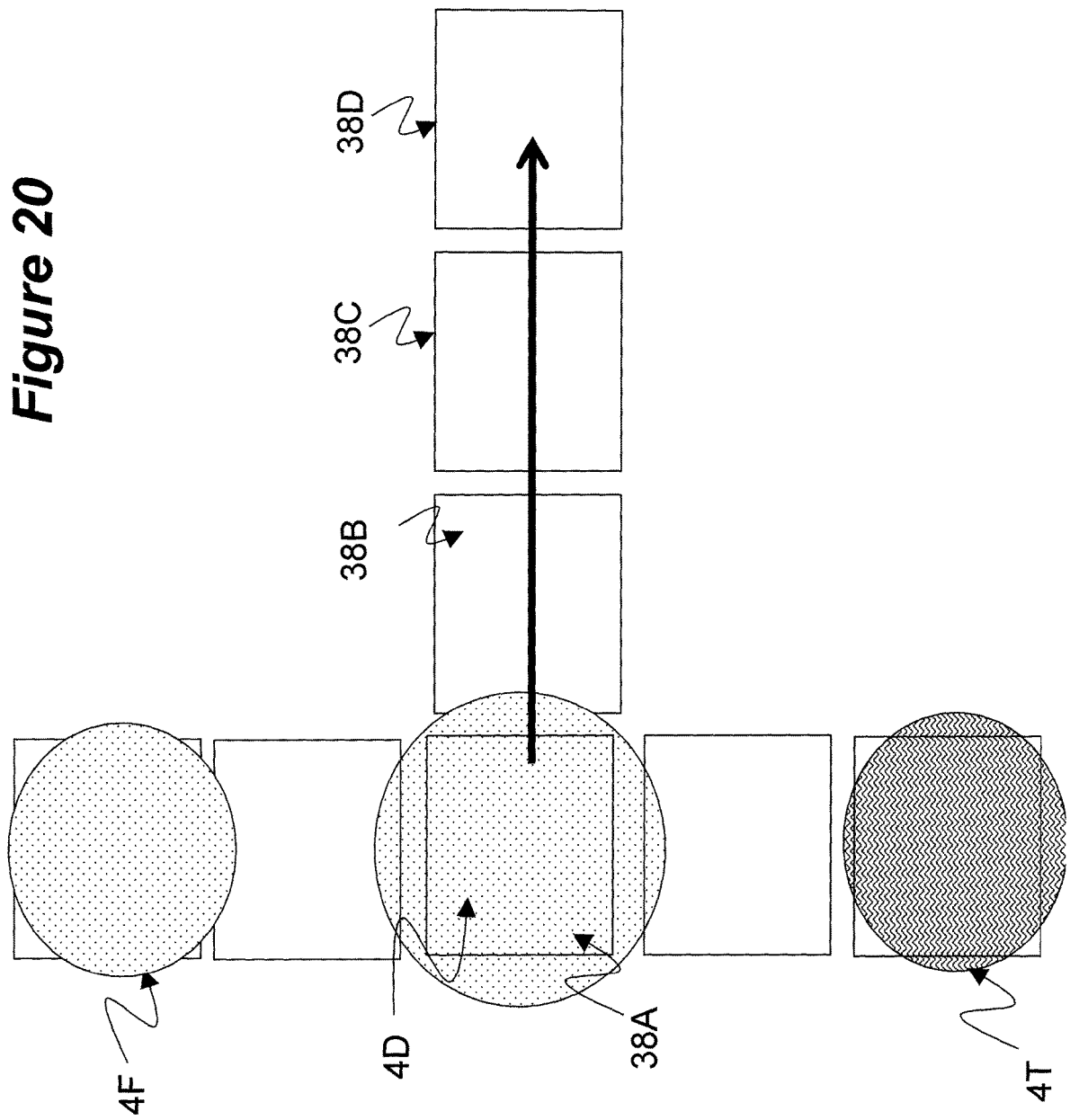
FIG. 20 shows a part of the AM-EWOD device of FIG. 3, and an exemplary protocol for performing an endotoxin assay according to a tenth embodiment of the invention.

An exemplary implementation is shown schematically in FIG. 20 which shows an exemplary protocol for detecting the presence of bacterial endotoxin in a sample droplet 4T. The sample droplet 4T and a LAL reagent droplet 4F are moved on the device to array element 38A, where they may be mixed together to form a product droplet 4D. The product droplet 4D may be held in position for a specified wait time whilst any chemical reaction may occur. The wait time may be a time in the range from 1 s to 3 hours, or in the range 10 s to 1 hour, or in the range 1 minute to 20 minutes, or around 10 minutes. During the wait time the device may be heated so that the product droplet is heated to a reaction temperature. The reaction temperature may be in the range 20° C. to 80° C. or in the range 30° C. to 50° C., or in the range 35° C. to 40° C. or around 37° C. Following the completion of the wait time, an attempt may be made to move the droplet by means of the electro-wetting force from element electrode 38A to element electrode 38D as indicated in FIG. 20. If the sample droplet 4T contained bacterial endotoxin above a certain threshold concentration, the chemical reaction occurring in the product droplet 4D may result in the formation of a gel clot within droplet 4D. As a result, in this situation, it may be impossible to transport the droplet to element electrode 4D. By contrast, if the sample droplet 4A contained no bacterial endotoxin, or bacterial endotoxin in small amounts below a certain critical concentration, no gel clot will be formed and the droplet will be successfully transported from element electrode 4A to element electrode 4D by means of the normal droplet movement protocol.

In this example, the principles of the first described embodiment have been applied to endotoxin detection using the LAL assay, and specifically the result of the assay is determined in accordance with whether product droplet 4D is in a movable or non-movable state.

Similarly the principles of the other described embodiments may be applied to determine the assay result based on any suitable dynamic property. For example, the reaction in the product droplet 4D may result in a change in the viscosity of the product droplet 4D. This change in viscosity may be measured by measuring the maximum speed at which the product droplet 4D can be transported on device, for example by applying the methods of the fifth embodiment. In another example, a viscosity change may be determined by studying the splitting properties of the product droplet 4D, as described, for example, in the second or sixth embodiments.

The reaction may also be performed in a differential manner, for example by employing the methods described for the $7^{th}$-$9^{th}$ embodiments, i.e., using one or more reference droplets and measuring additionally a corresponding dynamic property of one or more reference droplets.

Since the bacterial endotoxin assay typically uses natural products to manufacture the reagent droplets 4B, it may be particularly advantageous to extend the assay protocol so that additional reference reactions are performed on one or more additional reference droplets containing a known amount of endotoxin (controlled standard endotoxin, CSE). Optionally, the CSE may have a concentration that is pre-calibrated against the LAL reagent used to perform the assay using a negative or positive control. Optionally, a series of reference droplets may be created and measured, each containing different concentrations of CSE.

In such embodiments employing reference droplet reactions and an associated calibration curve (also known as a reference curve), LAL-based assay method may include the steps of: dispensing a plurality of reference LAL reagent droplets onto respective portions of the electrode array of the microfluidic device; dispensing at least one diluent droplet onto another portion of the electrode array of the microfluidic device; controlling actuation voltages applied to the electrode array of the microfluidic device to mix the references LAL reagent droplets with the at least one diluent droplet respectively to form a plurality of reaction droplets of different concentrations of reagent; generating a calibration curve based on the sensed dynamic property of the reaction droplets; plotting the sensed dynamic property of the product droplet on the calibration curve; and determining a result of the assay by the presence of bacterial endotoxin in the sample droplet based on the plot of the dynamic property of the product droplet on the calibration curve.

Figure 21:
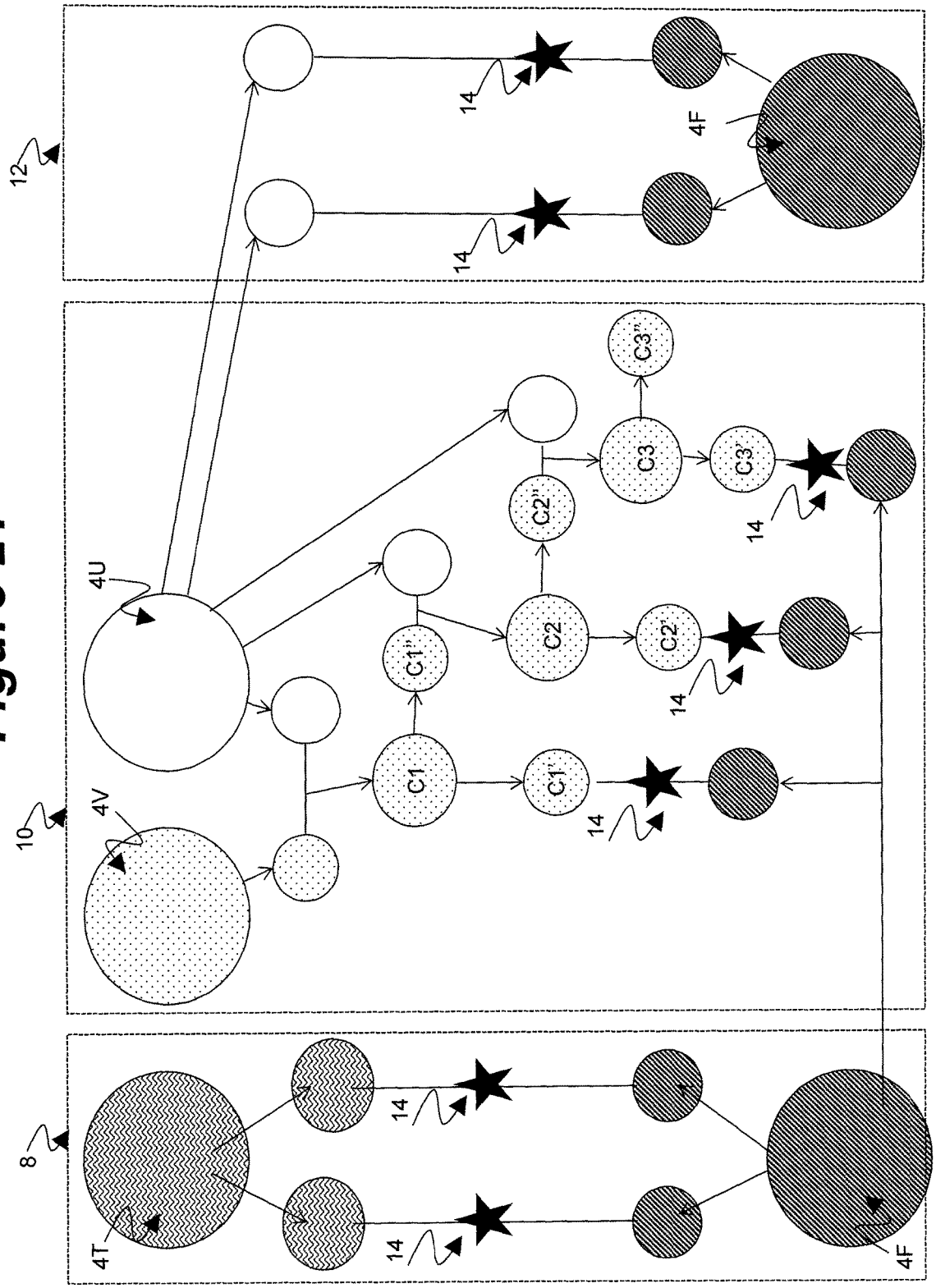
FIG. 21 shows a calibration protocol and a negative control that may be employed as part of the tenth embodiment of the invention.

An exemplary configuration for the entire reaction protocol including such a calibration protocol and a negative control in accordance with the tenth embodiment of the invention is shown in FIG. 21, and described as follows. Four chemical species participate in the protocol which may be dispensed onto the device in droplet format (there may be one or more droplets of each dispensed). The participating chemical species are:

A sample droplet 4T,

A LAL reagent droplet 4F,

A negative control standard droplet 4U, which may for example be comprised of diluent, or of some other material that does not react with LAL reagent, and A controlled standard endotoxin droplet 4X

The negative control standard droplet 4U may be comprised of diluent or some other material that is non-reactive with LAL reagent. Optionally and preferably the negative control standard droplet may be endotoxin free water and may be certified endotoxin free.

Smaller sub-droplets of each species may be created by splitting the larger input droplets as shown in FIG. 21 by the arrows. The reaction contains three branches, a sample reaction 8, calibration reactions 10 and negative control reaction 12. The creation of product droplets at a reaction point 14 is shown by the star symbol. At the reaction point 14, each of the created product droplets is measured by some means of determining a dynamic property of the product droplet as previously described. The assay protocol is implemented as follows:

In the sample reaction 8, a LAL reagent droplet 4F is reacted with a sample droplet 4T.

In the negative control reaction 12, a LAL reagent droplet 4F is reacted with a negative control standard droplet 4U.

In the calibration reaction, droplets of different dilutions of Controlled Standard Endotoxin are reacted with LAL reagent droplets 4. The reaction droplets of different concentrations (e.g. C1', C2', C3') may be created by serial dilution of the CSE reagent with the diluent water. An exemplary procedure, as shown in FIG. 21 involves:

Merging a droplet of CSE with a negative control standard droplet 4U (comprised of diluent water) to create a droplet C1.

Splitting droplet C1 into two halves, C1' and C1".

Droplet C1' thus created is used as a reaction droplet having 0.5×CSE concentration.

Droplet C1" is then further merged (diluted) with a droplet of diluent to create droplet C2.

Droplet C2 is split into two halves (C2' and C2").

Droplet C2' is used as a reaction droplet having 0.25× CSE concentration.

Droplet C2" is further merged (diluted) with a droplet of diluent to create a droplet C3.

Droplet C3 is split into two halves (C3' and C3").

Droplet C3' is used as a reaction droplet having 0.125× CSE concentration.

The reaction droplets C1', C2' and C3' may each be reacted with LAL reagent and the product droplets measured. In this way a calibration curve may be constructed.

In the example protocol of FIG. 21, the reference droplets C1' and C2' and C3' may be generated on the device. Such an arrangement is advantageous. Optionally, the same measurement may be made in duplicate or triplicate on different parts of the array within the same AM-EWOD device 41. For example, in FIG. 21 the sample reaction 8 and negative control reaction 12 are both shown conducted in duplicate. Optionally and preferably, sample reaction 8, negative control reaction 12 and calibration reactions 10 may all be conducted in duplicate, triplicate or quadruplicate. In the example protocol of FIG. 21 the calibration curve has been shown with calibrant droplets C1', C2' and C3' having CSE concentrations of ×0.5, ×0.25 and ×0.125 respectively. Optionally and preferably, the calibration may also be performed over a wider range of CSE concentrations, preferably within the range 0.0001 EU to 10 EU, or within the range 0.001 EU to 1 EU. Optionally and preferably, the calibrant droplets may have CSE concentrations that are roughly evenly spaced on a logarithmic scale. In the example protocol of FIG. 21, the calibrant droplets (C1', C2' and C3') are produced by successive dilutions of factor ×2, produced by merging droplets (e.g. C1" and C2") with diluent droplets of the same size. Optionally, a larger dilution ratio, such as ×10, may be effected by performing dilutions where the diluent droplet is larger than the CSE droplet. Optionally, and advantageously the size/volume of each droplet may be accurately measured by means of the AM-EWOD sensor function. Optionally the size/volume measurement information may be used to determine very precisely the concentration of CSE in each of the calibrant droplets.

Figure 22:
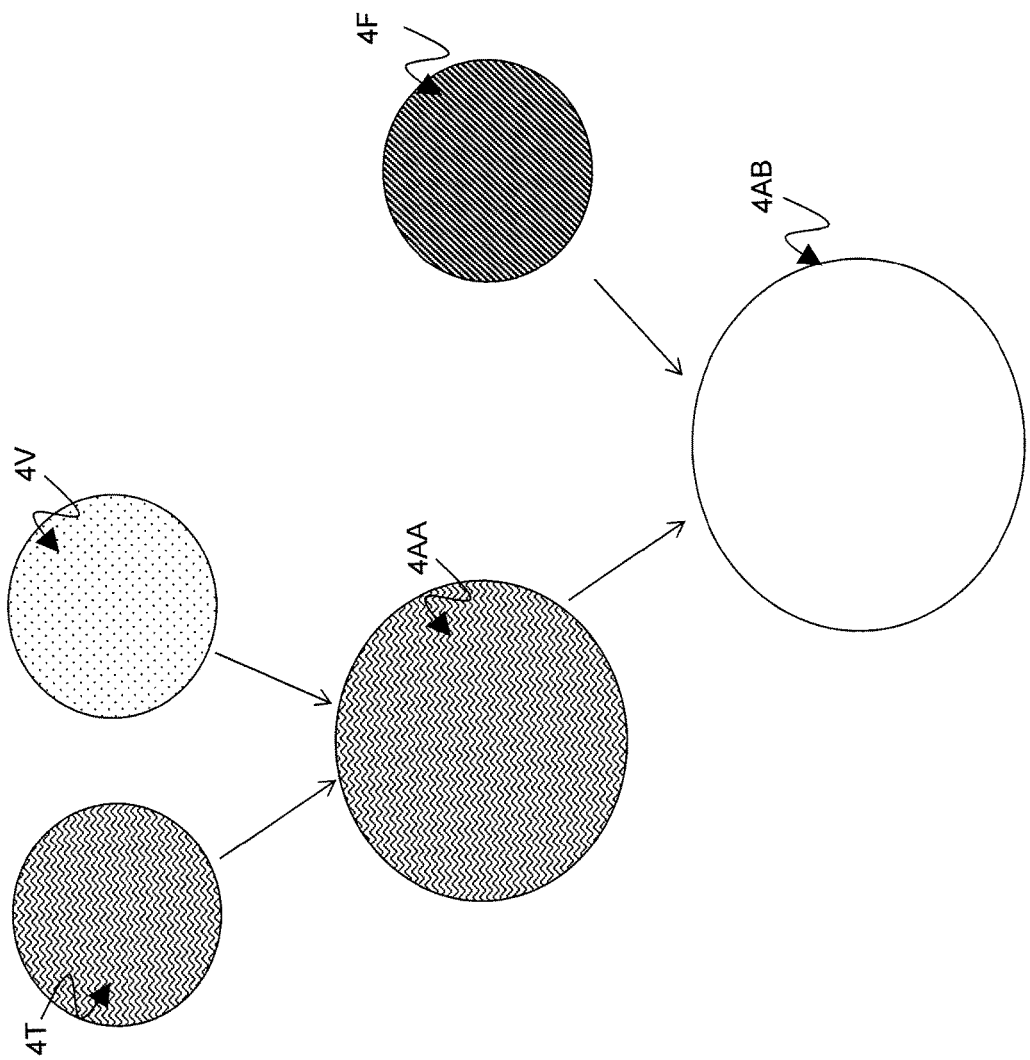
FIG. 22 shows a positive control that may be employed as part of the tenth embodiment of the invention.

Optionally the protocol of FIG. 21 may be further modified by the addition of a positive control branch of the reaction. This may comprise the additional further steps as shown in FIG. 22 of:

Combining a sample droplet 4T with a CSE droplet 4V to create a positive control reference droplet 4AA; and Combining the positive control reference droplet 4AA with a LAL reagent droplet 4F to create a positive control product droplet 4AB and monitoring the reaction as previously described.

A positive control reaction may be included in circumstances where it is desirable to verify, for example, whether any chemical species within the sample droplet has an accelerating or retarding effect on the rate of the chemical reaction.

It may be noted that in the standard terminology of the endoxotin testing industry the positive control may be referred to as a "positive product control", where the product in this case refers to a product (e.g. a pharmaceutical product) being the sample under test. In the language of this disclosure we have, in general, reserved the use of the product to describe the droplet created by the assay protocol described, and of which a dynamic property is sensed to determine the output of the assay.

Alternatively and optionally, the positive control may follow the above protocol where the sample droplet 4T is instead replaced by a droplet of a suitable diluent, for example endotoxin free water. In this case the positive control reference droplet is created by mixing the diluent droplet with the CSE droplet.

Alternatively and optionally both of the above types of positive control may be included.

Optionally and preferably, a suitable surfactant may be added to some or all of the droplets of sample, reagents, controlled standard endotoxin and diluent water. The use of a surfactant may have some or all of the benefits of improving droplet transport properties by lowering the surface tension of the droplets, and therefore also the electro-wetting voltage, of reducing surface contamination of the hydrophobic surfaces of the device or of increasing the speed of the reaction and therefore reducing the reaction time.

Optionally and preferably, the AM-EWOD device 41 and diluent water may be certified endotoxin free to eliminate environmental interference of the test result.

Optionally and preferably, the assay may be conducted with the droplets maintained at a temperature of around 37° C., for example by heating the droplets or by heating the cartridge.

An advantage of the tenth embodiment is that it describes methods of implementing an endotoxin assay in an AM-EWOD device 41. The advantages of this format for an endotoxin assay are:

Minimal quantities (typically ~1 uL or less) of sample and reagents are required in order to perform the assay. This may reduce the cost of the test since the LAL reagent is relatively expensive, and the sample may also be a material that is rare, expensive or precious.

The assay is performed in a microfluidic format with droplets. This may reduce the time to result since typically chemical reactions may occur more quickly in microfluidics. In particular, the time to formation of a gel clot may be significantly reduced in microfluidics compared to a macroscopic format (e.g. in a test tube).

Performing the assay in a microfluidic format may increase the sensitivity. Therefore, very small quantities of bacterial endotoxin may be detected.

The readout of the assay may be detected by electrical means, for example the droplet may be moved or not by electro-wetting action. Such a means of measurement is very repeatable and non-subjective, compared for example, to the determination of whether a gel clot has formed in a test tube. Additionally, by making the test non-subjective in this way, it may be implemented by an operator with only minimal training in how to use the device since all droplet operations are controlled automatically, for example by means of a pre-configured software file. This may have a further advantage in that the test can be performed by a relatively unskilled operator, since it is not necessary for the operator to have to make a judgment as to whether or not a clot has formed.

The AM-EWOD device 41 is an extremely convenient format for performing calibration and control measurements, for example by creating a number of reference droplets on the device and quantifying one or more of their dynamic properties, using any of the methods previously described. Thus, the result of the assay may be calibrated to a very high precision. Such means of calibration/providing reference measurement may be done in a completely automated way, by using the capability of the AM-EWOD device 41 to manipulate multiple droplets 4 simultaneously and in a configurable way. Similarly, calibration may be to a high degree of precision by exploiting the capability of the device to control and measure droplet volumes very accurately by using the integrated sensor function.

An eleventh embodiment of the invention is as the tenth embodiment except that the LAL assay chemistry may be modified to make the test specifically sensitive to (1,3)-beta-D-glucan (referred to as "glucans") and (optionally) also insensitive to bacterial endotoxin. This may be achieved by modifying the reagent chemistry to suppress the Factor B' pathway and to enable the Factor G' pathway of the lysate reaction, using the known means as described, for example, by references cited in the background art section.

The detection of glucans may find applications in clinical diagnostics, and in the detection of invasive fungal disease. Multiple studies have shown glucans to become elevated well in advance of conventional clinical signs and symptoms. The early diagnosis of fungal infection is associated with improved clinical outcome and is a value to clinicians. In contrast, delayed diagnosis and therapy of invasive fungal disease is associated with increased mortality. Hence, there is significant utility in the application of a glucans test in at-risk patients. Immunosuppressed patients are at high risk for developing invasive fungal disease, which is often difficult to diagnose. Affected patient populations include: cancer patients undergoing chemotherapy, stem cell and organ transplant patients, burn patients, HIV patients and ICU patients.

A test for glucans using the LAL reaction chemistry, resulting in the change of a dynamic property of a product droplet 4D, may be performed using any of the detection methods described in embodiments 1-9 to detect a change in droplet dynamic properties in the AM-EWOD device 41. Specifically the glucans assay chemistry may be arranged such that the product droplet 4D undergoes a clotting reaction or a viscosity change.

The example assay protocols for performing a glucans assay may be similar or identical to those previously described for the LAL assay and illustrated in FIGS. 20 and 21. More specifically, a glucan assay protocol may replace the Controlled Standard Endotoxin reagent with a corresponding reagent comprising a controlled quantity of glucans. Likewise, negative control and diluent reagents may be certified as glucan free. Likewise, the LAL reagent may be adapted so as to be sensitive to the presence of glucans and insensitive to the presence of endotoxin as previously described.

The implementation of a test for glucans in a cartridge containing a microfluidic AM-EWOD device 41 has the same advantages as already described for the tenth embodiment, and some additional advantages as follows:

The test may be implemented in a cheap and disposable microfluidic device and with a miniaturized (e.g. handheld) reader 40.

As such it may be suitable for application at Point of Care, for example in a doctors surgery, by a nurse on a ward round or by a healthcare professional in the home.

The advantages of point of care testing are rapid turn-around to results, low cost and ease and convenience of testing, all of which may lead to improved patient outcomes.

A twelfth embodiment of the invention utilizes the device and methods of any one of embodiments 1-9 in order to perform an assay for nucleic acid amplification.

According to a twelfth embodiment of the invention, the device and methods of any of previously described embodiments one to nine may be incorporated into an assay for performing nucleic acid amplification on device in a droplet format requiring no optical detection. The final result of the assay, i.e. whether a large quantity of the target DNA is present in the product droplet at the end of the reaction, may instead be determined by sensing a dynamic property of one or more product droplets at the culmination of the assay.

An advantage of the twelfth embodiment is that nucleic acid amplification may be sensed by electronic means (i.e. a change in a dynamic property of a droplet). There is therefore no need to sense the result of the assay optically. This has the advantage of simplifying the reader instrument since it is no longer required to include illumination and detection optics, for example for measuring the fluorescence properties of the droplet, as would conventionally be the case. A further advantage is that such an electronic means of detection may also simplify the assay chemistry since there is no longer a requirement to include probes within the assay chemistry as are conventionally added to facilitate optical readout.

A thirteenth embodiment of the invention utilizes the device and methods of any one of embodiments 1-9 in order to perform an assay for detecting the outcome of a coagulation assay. For example, the device and methods may be used to perform a thromboelastogram whereby the global visco-elastic properties of whole blood clot formation are determined.

According to the thirteenth embodiment of the invention, the device and methods of any of previously described embodiments one to nine may be incorporated into an assay for performing a coagulation assay on device in a droplet format requiring no optical detection. An example implementation may involve the mixing of a droplet of sample (for example blood, or a component derived from blood) with a chemical for causing coagulation. The ability of the blood to coagulation and/or its change in viscosity over time may be measured by monitoring a dynamic property of the product droplet, for example as previously described. An advantage of the thirteenth embodiment is that such a method of performing a coagulation assay may be implemented on a microfluidic AM-EWOD device 41

A fourteenth embodiment of the invention utilizes the device and methods of any one of embodiments 1-9 in order to perform an assay for measuring the viscosity of an industrially produced chemical. Such a test may be performed in an AM-EWOD device 41, for example at a location adjacent to the production line or in quality control. An advantage of the fourteenth embodiment is that such a test may be implemented on only a small quantity of sample. This may be particularly advantageous if the sample is precious or expensive, for example in the fabrication of biochemical or chemical reagents.

Whilst in the preceding embodiments the invention has been described in terms of an AM-EWOD device 41, utilizing integrated thin film electronics 74 and an integrated impedance sensor capability, it will also be appreciated that the invention could alternatively be implemented with a standard EWOD device by using an alternative means on sensing droplet position. For example, a CCD camera could be used to measure the droplet position and relay this information to the control electronics. Alternatively, the EWOD device could incorporate a sensing method as described in U.S. Pat. No. 8,653,832 (and referenced in the background section) for detecting droplet position.

Whilst in the preceding embodiments, the invention has been described in terms of an AM-EWOD device 41 utilizing thin film electronics 74 to implement array element circuits and driver systems in thin film transistor (TFT) technology, the invention could equally be realized using other standard electronic manufacturing processes, e.g. Complementary Metal Oxide Semiconductor (CMOS), bipolar junction transistors (BJTs), and the like.

A fourteenth embodiment of the invention is as any of the previous embodiments, where the droplet microfluidic device is of a non-EWOD type. The device could for example be based on a continuous flow system, for example as described in the paper by Teh et al. referenced in the background section. In this embodiment, a dynamic property of the droplet within a continuous flow channel may be modified according to the result of the assay. Examples of dynamic properties may include, but are not limited to any one or more of the following:

The ability of the droplets to coalesce with other droplets when they are converged together.
The viscosity of the droplets, which may be measured for example be measured by their deformation when subject to a flow of surrounding fluid in a transverse direction to the direction of movement.
The stability of the droplets and their propensity to break up.
The ability of the droplets to stick to a sidewall surface with which they may come into contact.

The fourteenth embodiment has similar advantages to the previously described embodiments applied to a system utilizing non-EWOD droplet microfluidics.

An aspect of the invention, therefore, is a method of determining a result of an assay in a microfluidic device. In exemplary embodiments, the method of determining a result of an assay may include the steps of: dispensing a sample droplet onto a first portion of an electrode array of the microfluidic device; dispensing a reagent droplet onto a second portion of the electrode array of the microfluidic device; controlling actuation voltages applied to the electrode array of the microfluidic device to mix the sample droplet and the reagent droplet into a product droplet; sensing a dynamic property of the product droplet; and determining the result of the assay of the sample droplet based on the sensed dynamic property. Such method may include one or more of following features, either individually or in combination.

In an exemplary embodiment of the method of determining a result of an assay, the dynamic property of the product droplet is a physical property of the product droplet that influences a transport property of the product droplet on the electrode array of the microfluidic device.

In an exemplary embodiment of the method of determining a result of an assay, the method further includes actuating a portion of the electrode array associated with the product droplet, wherein the transport property of the product droplet is whether the product droplet is in a moveable or non-moveable state with the actuation of the electrode array portion.

In an exemplary embodiment of the method of determining a result of an assay, the method further includes adjusting an actuation voltage of the electrode array portion in multiple steps to determine a minimum actuation voltage to render the product droplet into the moveable state from the non-moveable state.

In an exemplary embodiment of the method of determining a result of an assay, the method further includes adjusting a temperature of the electrode array portion in multiple steps to determine a minimum temperature to render the product droplet into the moveable state from the non-moveable state.

In an exemplary embodiment of the method of determining a result of an assay, the method further includes actuating a portion of the electrode array associated with the product droplet, wherein the transport property of the product droplet is whether the product droplet may be split into daughter droplets by the actuation of the electrode array portion.

In an exemplary embodiment of the method of determining a result of an assay, the method further includes adjusting an actuation voltage applied to the electrode array portion in multiple steps to determine a minimum actuation voltage to render the product droplet into a split-able state from a non-split-able state.

In an exemplary embodiment of the method of determining a result of an assay, the method further includes adjusting a temperature of the electrode array portion in multiple steps to determine a minimum temperature to render the product droplet into a split-able state from a non-split-able state.

In an exemplary embodiment of the method of determining a result of an assay, the method further includes actuating a portion of the electrode array associated with the product droplet, wherein the transport property of the product droplet is a maximum average speed of movement of the product droplet across the electrode array portion by actuation of the electrode array portion.

In an exemplary embodiment of the method of determining a result of an assay, the transport property of the product droplet is related to a viscosity of the product droplet.

In an exemplary embodiment of the method of determining a result of an assay, the method further includes actuating a portion of the electrode array associated with the product droplet to split the product droplet into daughter droplets, wherein the viscosity of the droplet is determined based on sensing a distance between centroids of the daughter droplets at a time of splitting of the product droplet by actuation of the electrode array portion.

In an exemplary embodiment of the method of determining a result of an assay, the method further includes actuating a portion of the electrode array associated with the product droplet, wherein the viscosity of the droplet is determined based on a time to effect a splitting of the product droplet by actuation of the electrode array portion.

In an exemplary embodiment of the method of determining a result of an assay, the method further includes the steps of: dispensing a first reagent droplet on the second portion of the electrode array of the microfluidic device; controlling actuation voltages applied to the electrode array of the microfluidic device to mix the sample droplet and the first reagent droplet into an intermediate product droplet; dispensing a second reagent droplet onto a third portion of the electrode array of the microfluidic device; and controlling actuation voltages applied to the electrode array of the microfluidic device to mix the intermediate product droplet and the second reagent droplet into the product droplet.

In an exemplary embodiment of the method of determining a result of an assay, the method further includes dispensing a reference droplet onto another portion of the electrode array; sensing the dynamic property of the reference droplet; and determining the result of the assay of the sample droplet by comparing the sensed dynamic property of the product droplet to the sensed dynamic property of the reference droplet.

In an exemplary embodiment of the method of determining a result of an assay, the method further includes dispensing multiple reference droplets onto respective portions of the electrode array; sensing the dynamic property of the reference droplets; generating a calibration curve based on the sensed dynamic property of the reference droplets; plotting the sensed dynamic property of the product droplet on the calibration curve; and determining the result of the assay of the sample droplet based on the plot of the dynamic property of the product droplet on the calibration curve.

In an exemplary embodiment of the method of determining a result of an assay, determining the result of the assay of the sample droplet comprises determining whether a chemical species is present in the sample droplet.

In an exemplary embodiment of the method of determining a result of an assay, the assay comprises a nucleic acid amplification assay, and determining the result of the assay of the sample droplet comprises determining whether a target quantity of nucleic acid is present in the assay.

In an exemplary embodiment of the method of determining a result of an assay, the assay comprises a blood coagulation assay, and determining the result of the assay of the sample droplet comprises determining whether a clot has formed based on the sensed dynamic property.

Another aspect of the invention is an assay measurement system for determining a result of an assay. In exemplary embodiments, the assay measurement system includes: a microfluidic device including an electrode array configured to receive fluid droplets; a controller configured to control actuation voltages applied to the electrode array to perform manipulation operations to the fluid droplets; and a sensor for sensing a dynamic property of the fluid droplets as a result of the manipulation operations. In addition, a sample droplet is dispensed onto a first portion of the electrode array; a reagent droplet is dispensed onto a second portion of the electrode array; the controller controls actuation voltages applied to the electrode array to mix the sample droplet and the reagent droplet into a product droplet; the sensor senses a dynamic property of the product droplet; and the controller further is configured to determine a result of the assay based on the sensed dynamic property of the product droplet.

In an exemplary embodiment of the assay measurement system, the sensor is an integrated sensor that is integrated into array element circuitry of the electrode array of the microfluidic device.

Although the invention has been shown and described with respect to a certain embodiment or embodiments, equivalent alterations and modifications may occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein exemplary embodiment or embodiments of the invention. In addition, while a particular feature of the invention may have been described above with respect to only one or more of several embodiments, such feature may be combined with one or more other features of the other embodiments, as may be desired and advantageous for any given or particular application.

Optionally, the device may also be arranged such that embodiments of the invention may be utilized in just a part or sub-array of the entire device. Optionally, some or all of the multiple different embodiments may be utilized in different rows columns or regions of the device.

INDUSTRIAL APPLICABILITY

The described embodiments could be used to provide an enhance AM-EWOD device. The AM-EWOD device could form a part of a lab-on-a-chip system. Such devices could be used in manipulating, reacting and sensing chemical, biochemical or physiological materials. Applications include healthcare diagnostic testing, material testing, chemical or biochemical material synthesis, proteomics, tools for research in life sciences and forensic science.

What is claimed is:

1. A method of determining a result of an assay in an active matrix electrowetting on dielectric (AM-EWOD) microfluidic device comprising the steps of:
   dispensing a sample droplet from a sample reservoir onto a first portion of an electrode array of the microfluidic device;
   dispensing a reagent droplet from a reagent reservoir onto a second portion of the electrode array of the microfluidic device;
   controlling actuation voltages applied to the electrode array of the microfluidic device to mix the sample droplet and the reagent droplet into a product droplet;
   sensing a dynamic property of the product droplet, wherein a dynamic property is a physical property of the product droplet that influences droplet transport on the microfluidic device, and a chemistry of the assay being performed is chosen such that the product droplet has the dynamic property depending on the result of the assay being performed;
   wherein sensing the dynamic property includes the steps of:
      controlling actuation voltages applied to the product droplet to affect a droplet transport operation at a first position on the electrode array on the microfluidic device, and sensing the product droplet with a first sensor at the first position;
      sensing the product droplet with a second sensor at a second position on the electrode array on the microfluidic device different from the first position; and
      executing application software with control electronics to automatically determine the sensed dynamic property based on a result of the droplet transport operation using transport measurements sensed by the first and second sensors; and
   executing application software with the control electronics to automatically determine the result of the assay of the sample droplet directly from the sensed dynamic property by equating either a positive or negative result for a target species in the sample droplet to the result of the transport operation.

2. The method of determining a result of an assay of claim 1, further comprising actuating a portion of the electrode array associated with the product droplet, wherein the transport property of the product droplet is whether the product droplet is in a moveable or non-moveable state with the actuation of the electrode array portion.

3. The method of determining a result of an assay of claim 2, further comprising adjusting an actuation voltage of the electrode array portion in multiple steps to determine a minimum actuation voltage to render the product droplet into the moveable state from the non-moveable state.

4. The method of determining a result of an assay of claim 2, further comprising adjusting a temperature of the electrode array portion in multiple steps to determine a minimum temperature to render the product droplet into the moveable state from the non-moveable state.

5. The method of determining a result of an assay of claim 1, further comprising actuating a portion of the electrode array associated with the product droplet, wherein the transport property of the product droplet is whether the product droplet may be split into daughter droplets by the actuation of the electrode array portion.

6. The method of determining a result of an assay of claim 5, further comprising adjusting an actuation voltage applied to the electrode array portion in multiple steps to determine a minimum actuation voltage to render the product droplet into a split-able state from a non-split-able state.

7. The method of determining a result of an assay of claim 5, further comprising adjusting a temperature of the electrode array portion in multiple steps to determine a minimum temperature to render the product droplet into a split-able state from a non-split-able state.

8. The method of determining a result of an assay of claim 1, wherein the transport property of the product droplet is related to a viscosity of the product droplet.

9. The method of determining a result of an assay of claim 8, further comprising actuating a portion of the electrode array associated with the product droplet to split the product droplet into daughter droplets, wherein the viscosity of the droplet is determined based on sensing a distance between centroids of the daughter droplets at a time of splitting of the product droplet by actuation of the electrode array portion.

10. The method of determining a result of an assay of claim 8, further comprising actuating a portion of the electrode array associated with the product droplet, wherein the viscosity of the droplet is determined based on a time to effect a splitting of the product droplet by actuation of the electrode array portion.

11. The method of determining a result of an assay of claim 1, further comprising the steps of:
dispensing a first reagent droplet on the second portion of the electrode array of the microfluidic device;
controlling actuation voltages applied to the electrode array of the microfluidic device to mix the sample droplet and the first reagent droplet into an intermediate product droplet;
dispensing a second reagent droplet onto a third portion of the electrode array of the microfluidic device; and
controlling actuation voltages applied to the electrode array of the microfluidic device to mix the intermediate product droplet and the second reagent droplet into the product droplet.

12. The method of determining a result of an assay of claim 1, further comprising:
dispensing a reference droplet onto another portion of the electrode array; sensing the dynamic property of the reference droplet; and
determining the result of the assay of the sample droplet by comparing the sensed dynamic property of the product droplet to the sensed dynamic property of the reference droplet.

13. The method of determining a result of an assay of claim 12, further comprising:
dispensing multiple reference droplets onto respective portions of the electrode array;
sensing the dynamic property of the reference droplets;
generating a calibration curve based on the sensed dynamic property of the reference droplets;
plotting the sensed dynamic property of the product droplet on the calibration curve; and
determining the result of the assay of the sample droplet based on the plot of the dynamic property of the product droplet on the calibration curve.

14. The method of determining a result of an assay of claim 1, wherein determining the result of the assay of the sample droplet comprises determining whether a chemical species is present in the sample droplet.

15. The method of determining a result of an assay of claim 1, wherein the assay comprises a nucleic acid amplification assay, and determining the result of the assay of the sample droplet comprises determining whether a target quantity of nucleic acid is present in the assay.

16. The method of determining a result of an assay of claim 1, wherein the assay comprises a blood coagulation assay, and determining the result of the assay of the sample droplet comprises determining whether a clot has formed based on the sensed dynamic property.

17. An assay measurement system for determining a result of an assay, the assay measurement system comprising:
a microfluidic device including an electrode array configured to receive fluid droplets;
a controller configured to control actuation voltages applied to the electrode array to perform manipulation operations to the fluid droplets; and
a plurality of sensors for sensing a dynamic property of the fluid droplets as a result of the manipulation operations:
wherein:
a sample droplet is dispensed onto a first portion of the electrode array;
a reagent droplet is dispensed onto a second portion of the electrode array;
the controller controls actuation voltages applied to the electrode array to mix the sample droplet and the reagent droplet into a product droplet;
a dynamic property is a physical property of the product droplet that influences droplet transport on the microfluidic device, and a chemistry of the assay being performed is chosen such that the product droplet has the dynamic property depending on the result of the assay being performed;
the controller is configured to control actuation voltages applied to the product droplet to affect a droplet transport operation at a first position on the electrode array on the microfluidic device;
the plurality of sensors includes a first sensor that senses the product droplet at the first position;
the plurality of sensors includes a second sensor that senses the product droplet at a second position on the electrode array on the microfluidic device different from the first position;
the controller is configured to execute application software to automatically determine the sensed dynamic property based on a result of the droplet transport operation using transport measurements sensed by the first and second sensors; and
the controller is configured to execute application software to automatically determine the result of the assay of the sample droplet directly from the sensed dynamic property by equating either a positive or negative result for a target species in the sample droplet to the result of the transport operation.

18. The assay measurement system of any of claim 17, wherein the plurality of sensors includes an integrated sensor that is integrated into array element circuitry of the electrode array of the microfluidic device.

19. A method of determining a result of an assay in an active matrix electrowetting on dielectric (AM-EWOD) microfluidic device comprising the steps of:
dispensing a sample droplet from a sample reservoir onto a first portion of an electrode array of the microfluidic device;
dispensing a reagent droplet from a reagent reservoir onto a second portion of the electrode array of the microfluidic device;
controlling actuation voltages applied to the electrode array of the microfluidic device to mix the sample droplet and the reagent droplet into a product droplet;
sensing a dynamic property of the product droplet, wherein a dynamic property is a physical property of the product droplet that influences droplet transport on the microfluidic device, and the dynamic property depends on the result of the assay being performed;
wherein sensing the dynamic property includes the steps of:
controlling actuation voltages applied to the product droplet to affect a droplet transport operation at a first position on the electrode array on the microfluidic device, and sensing the product droplet with a first sensor at the first position;
sensing the product droplet with a second sensor at a second position on the electrode array on the microfluidic device different from the first position; and
executing application software with control electronics to automatically determine the sensed dynamic property based on a result of the droplet transport operation using transport measurements sensed by the first and second sensors; and
executing application software with the control electronics to automatically determine the result of the assay of the sample droplet directly from the sensed dynamic property by equating either a positive or negative result for a target species in the sample droplet to the result of the transport operation;
wherein the transport property of the product droplet is related to a viscosity of the product droplet; and
the method further comprises actuating a portion of the electrode array associated with the product droplet to split the product droplet into daughter droplets, wherein the viscosity of the droplet is determined based on sensing a distance between centroids of the daughter droplets at a time of splitting of the product droplet by actuation of the electrode array portion.

\* \* \* \* \*